US012577190B2

(12) United States Patent
Lochmann et al.

(10) Patent No.: US 12,577,190 B2
(45) Date of Patent: *Mar. 17, 2026

(54) METHOD FOR PRODUCING POLYOL-BASED ESTERS OF KETOCARBOXYLIC ACIDS

(71) Applicant: KetoLipix Therapeutics GmbH, Hamburg (DE)

(72) Inventors: Dirk Lochmann, Witten (DE); Sebastian Reyer, Witten (DE); Michael Stehr, Witten (DE)

(73) Assignee: KetoLipix Therapeutics GmbH, Hamburg (DE)

( * ) Notice: Subject to any disclaimer, the term of this patent is extended or adjusted under 35 U.S.C. 154(b) by 838 days.

This patent is subject to a terminal disclaimer.

(21) Appl. No.: 17/618,594

(22) PCT Filed: Jun. 12, 2019

(86) PCT No.: PCT/EP2019/065268

§ 371 (c)(1),
(2) Date: Dec. 13, 2021

(87) PCT Pub. No.: WO2020/249195

PCT Pub. Date: Dec. 17, 2020

(65) Prior Publication Data

US 2022/0380289 A1 Dec. 1, 2022

(51) Int. Cl.
*C07C 67/03* (2006.01)
*A23L 33/10* (2016.01)

(52) U.S. Cl.
CPC .............. *C07C 67/03* (2013.01); *A23L 33/10* (2016.08)

(58) Field of Classification Search
CPC ................................ C07C 67/03; A23L 33/10
See application file for complete search history.

(56) References Cited

U.S. PATENT DOCUMENTS

2009/0197952 A1* 8/2009 Hashim et al. ........ A61K 31/22 514/522
2012/0137448 A1* 6/2012 Panandiker et al. ..... C11D 3/60 8/137

OTHER PUBLICATIONS

J. Am. Oil. Chem. Soc. 1995, 72, 61-65 (Charlemagne et al.) (Year: 1995).*

* cited by examiner

*Primary Examiner* — Amy C Bonaparte
*Assistant Examiner* — Derek Rhoades
(74) *Attorney, Agent, or Firm* — Brannon Sowers & Cracraft PC; Edward E. Sowers

(57) ABSTRACT

The invention relates to a method for producing polyol esters, especially polyglycerol esters, of 3-oxobutyric acid, as well as the products thus obtained and their use.

14 Claims, No Drawings

METHOD FOR PRODUCING POLYOL-BASED ESTERS OF KETOCARBOXYLIC ACIDS

CROSS-REFERENCES TO RELATED APPLICATIONS

This application is a National Stage filing of International Application PCT/EP 2019/065268 filed Jun. 12, 2019, entitled "METHOD FOR PRODUCING POLYOL-BASED ESTERS OF KETOCARBOXYLIC ACIDS". The subject application claims priority to PCT/EP 2019/065268 and incorporates all by reference herein, in its entirety.

BACKGROUND OF THE INVENTION

The present invention relates to the field of keto bodies and related metabolism and the therapy of related diseases.

Especially, the present invention relates to a method for producing polyol esters of 3-oxobutyric acid (synonymously also referred to as "3-oxobutanoic acid", "beta-oxobutyric acid", "beta-oxobutanoic acid", etc.), especially polyglycerol esters of 3-oxobutyric acid, as well as the reaction products thus obtainable or thus produced (i.e. polyol esters of 3-oxobutyric acid, especially polyglycerol esters of 3-oxobutyric acid) and their functionalized derivatives as well as their use, especially in pharmaceutical compositions, such as drugs or medicaments, or in food and/or food products, as well as their further applications or uses.

Furthermore, the present invention relates to pharmaceutical compositions, especially drugs or medicaments, comprising the reaction products (i.e. polyol esters of 3-oxobutyric acid, especially polyglycerol esters of 3-oxobutyric acid) obtainable or produced according to the inventive method, as well as their applications or uses.

Finally, the present invention relates to food and/or food products, especially food supplements, functional foods, novel foods, food additives, food supplements, dietary foods, power snacks, appetite suppressants and strength and/or endurance sports supplements, which comprise the reaction products (i.e. polyol esters, especially polyglycerol esters, of 3-oxobutyric acid or their functionalized derivatives) obtainable or produced according to the inventive method, as well as their applications or uses.

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called "ketone bodies" or "ketone bodies" in English).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetoacetate or 3-oxobutyrate) and acetone as well as 3-hydroxybutyric acid (hereinafter also synonymously referred to as beta-hydroxybutyric acid or BHB or 3-BHB) or its salt (i.e. 3-hydroxybutyrate or beta-hydroxybutyrate).

These keto bodies are also provided physiologically in large amounts from lipids stored in the body by lipolysis during fasting or starvation and replace the energy source glucose almost completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoA-synthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol from acetoacetate by the enzyme D-beta-hydroxybutyrate dehydrogenase. HMG-CoA is also an end product of the degradation of the amino acid leucine, while acetoacetate is formed during the degradation of the amino acids phenylalanine and tyrosine.

Acetoacetate is thus reductively converted under physiological conditions into the physiologically relevant form of 3-hydroxybutyric acid or 3-hydroxybutyrate.

3-Hydroxybutyric acid itself is currently used and marketed in the weight training sector as a sodium, magnesium or calcium salt.

However, 3-hydroxybutyric acid itself is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect.

In addition, the plasma half-life of 3-hydroxybutyric acid and its salts is so short that even if several grams are taken, the ketosis lasts only for about three to four hours, i.e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i.e. the metabolic conversion of caproic, caprylic and capric acid (i.e. of saturated linear $C_6$-, $C_8$- and $C_{10}$-fatty acids) from the corresponding triglycerides is intended.

Basically, however, from a pharmaceutical and clinical point of view, acetoacetate as the physiological precursor of 3-hydroxybutyric acid is a more effective pharmaceutical-pharmacological target molecule, which, according to the prior art, could in principle be used for the therapy of a large number of diseases (e.g. in diseases in connection with a malfunction of the energy metabolism, especially keto-body metabolism, or neurodegenerative diseases such as dementia, Alzheimer's disease, Parkinson's disease, etc., lipometabolic diseases etc.), but cannot be used due to its lack of physiological compatibility.

The following table illustrates purely exemplary, but by no means limiting, potential therapy options or possible indications for the active ingredient acetoacetate or 3-hydroxybutyric acid or its salt (i.e. 3-hydroxybutyrate), which is obtainable by physiological reduction of acetoacetate.

| Indication | Therapeutic effect |
|---|---|
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance. BHB offers an immediately effective alternative here. |
| Alzheimer's disease, dementia | Under BHB patients show better cognitive performance. BHB is also effective in the prevention of neurodegenerative diseases. |
| Disorders of fatty acid oxidation (e.g. electron transfer protein defect) | Compensation of a nutrient deficiency in case of defect in energy metabolism. |

Therefore, it is desirable from a pharmaceutical and clinical point of view to be able to find effective precursors or metabolites which physiologically allow director indirect access to acetoacetate (and thus physiologically also to 3-hydroxybutyric acid or its salts), especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

The problem underlying the present invention is thus the provision of an efficient method for producing physiologically suitable or physiologically compatible precursors and/or metabolites of acetoacetate or eventually 3-hydroxybutyric acid (i.e. beta-hydroxybutyric acid or BHB or 3-BHB) or their salts.

Such method should especially make the acetoacetate or respective BHB precursors and/or BHB metabolites accessible in an efficient way, especially in larger quantities and without significant amounts of toxic by-products.

BRIEF SUMMARY OF THE INVENTION

In a completely surprising way, the applicant has now discovered that polyol esters, especially polyglycerol esters, of 3-oxobutyric acid represent an efficient and physiologically effective or physiologically compatible precursor and/or metabolite for the keto body acetoacetate or 3-hydroxybutyric acid, which is reductively produced therefrom under physiological conditions, or its salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing polyol esters, especially polyglycerol esters, of 3-oxobutyric acid; further, especially special and/or advantageous embodiments of this inventive method are provided.

Moreover, the present invention relates—according to a second aspect of the present invention—to a method for producing of functionalized, especially fatty acid functionalized, polyol esters, especially polyglycerol esters, of 3-oxobutyric acid (beta-oxobutyric acid, 3-oxobutanoic acid), especially special and/or advantageous embodiments of this inventive method are disclosed.

Furthermore, the present invention relates—according to a third aspect of the present invention—to a reaction product obtainable according to the inventive method provided or a polyol ester, especially polyglycerol ester, of 3-oxo butyric acid (beta-oxobutyric acid, 3-oxobutanoic acid) or mixtures thereof similarly provided; further, especially special and/or advantageous embodiments of this aspect of the invention are provided.

Likewise, the present invention—according to a fourth aspect of the present invention—relates to a pharmaceutical composition, especially a drug or medicament; further, especially special and/or advantageous embodiments of this aspect of the invention are provided.

Furthermore, the present invention—according to a fifth aspect of the present invention—relates to an inventive reaction product or an inventive polyol ester, especially polyglycerol ester, of 3-oxobutyric acid (beta-oxobutyric acid, 3-oxobutanoic acid) or a mixture thereof for the prophylactic and/or therapeutic treatment or for use in the prophylactic and/or therapeutic treatment of diseases of the human or animal body.

Furthermore, the present invention—according to a sixth aspect of the present invention—relates to the use of an inventive reaction product or an inventive polyol ester, especially polyglycerol ester, of 3-oxobutyric acid (beta-oxobutyric acid, 3-oxobutanoic acid) or a mixture thereof for the prophylactic and/or therapeutic treatment or for producing a medicament for the prophylactic and/or therapeutic treatment of diseases of the human or animal body.

Furthermore, the present invention—according to a seventh aspect of the present invention—relates to the use of an inventive reaction product or an inventive polyol ester, especially polyglycerol ester, of 3-oxobutyric acid (beta-oxobutyric acid, 3-oxobutanoic acid) or a mixture thereof.

Furthermore, the present invention—according to an eighth aspect of the present invention—relates to a food and/or food product; further, especially special and/or advantageous embodiments of the food and/or food product are provided.

Finally, the present invention—according to a ninth aspect of the present invention—relates to the use of an inventive reaction product or an inventive polyol ester, especially polyglycerol ester, of 3-oxo butyric acid (beta-oxobutyric acid, 3-oxobutanoic acid) or mixtures thereof in a food and/or a food product; further, especially special and/or advantageous embodiments of the use are provided.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 100% or 100% by weight, respectively, including all components or ingredients, especially as defined below; however, this is self-evident for the person skilled in the art.

In addition, the skilled person may, if necessary, deviate from the following range specifications without leaving the scope of the present invention.

Additionally, it applies that all values or parameters or the like specified in the following can be determined or identified in principle with standardized or explicitly specified determination methods or otherwise with the determination or measurement methods that are otherwise familiar to a person skilled in the art Having stated this, the present invention will be described in more detail hereinafter:

DETAILED DESCRIPTION OF THE INVENTION

The subject-matter of the present invention—according to a first aspect of the present invention—is thus a method for producing polyol esters, especially polyglycerol esters, of 3-oxobutyric acid (beta-oxobutyric acid, 3-oxobutanoic acid), wherein at least one compound of the general formula (I)

$$CH_3—C(O)—CH_2—C(O)OR^1 \quad (I)$$

wherein, in the general formula (I), the radical $R^1$ represents $C_1$-$C_4$-alkyl, especially methyl or ethyl, preferably ethyl, is reacted with at least one polyol (II) comprising at least two, especially at least three, hydroxyl groups (OH groups), especially polyglycerol, so that, as a reaction product, one or more 3-oxobutyric acid polyol esters (III), especially 3-oxobutyric acid polyglycerol esters, are obtained.

As stated above, the applicant has, quite surprisingly, discovered that the polyol esters, especially polyglycerol esters, of 3-oxobutyric acid (beta-oxobutyric acid, 3-oxobutanoic acid)—synonymously also referred to as "3-oxobutyric acid polyol esters, especially 3-oxobutyric acid polyglycerol esters"—thus produced are efficient, since physiologically compatible precursors and/or metabolites of 3-hydroxybutyric acid or its salts, which can also be used in larger quantities in pharmaceutical or clinical applications because they are physiologically compatible.

The above-mentioned polyol esters, especially polyglycerol esters, of 3-oxobutyric acid, which are accessible for the first time in an efficient manner through the production method according to the invention, represent a physiologically and pharmacologically relevant alternative to free 3-hydroxybutyric acid or its salts.

The production of polyol esters, especially polyglycerol esters, of 3-oxobutyric acid by means of conventional organic synthesis is complex and costly, since 3-oxobutyric acid is unstable and decomposes. Within the scope of the present invention, it was possible for the first time to provide an efficiently working production method with which polyol esters, especially polyglycerol esters, of 3-oxobutyric acid can be produced without undesired side reactions, especially in a single step.

The inventive method thus makes it possible for the first time to provide non-toxic polyol esters, especially polyglycerol esters, of 3-oxobutyric acid from known, commercially available and above all physiologically harmless components or reactants (starting compounds). The resulting polyol esters, especially polyglycerol esters, of 3-oxobutyric acid can be broken down physiologically, especially in the stomach and/or bowl, and release or generate the target molecule "acetoacetate (acetoacetate)" ultimately from this "3-hydroxybutyric acid" or its salts as active ingredient or active component.

In addition, the aforementioned polyol esters, especially polyglycerol esters, of 3-oxobutyric acid also comprise an acceptable taste to ensure compatibility even when administered orally in larger quantities over a longer period of time (e.g. administration of 50 g daily dose or more).

Similarly, the production method according to the invention makes it possible to provide the polyol esters, especially polyglycerol esters, of 3-oxobutyric acid free from toxic impurities.

In addition, the production method according to the invention, including optional further processing or purification steps, can be operated economically and can also be implemented on a large scale.

Especially, the inventive production method uses commercially available starting compounds, which allow an economically efficient and furthermore a relatively simple process management, even in case of large-scale implementation.

In contrast to conventional prior art production methods, the production method according to the invention does not use complex starting materials and uses only a single step. Nevertheless, excellent yields are achieved in accordance with the invention, wherein the formation of by-products is minimized or avoided. Especially, due to the inventively used reactants to form 3-hydroxybutyric acid precursors or metabolites, dimerization can be prevented.

In addition, the inventive method is simple and economical. Especially, the method according to the invention is usually carried out in the absence of solvents and/or without any solvent (i.e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

The production method according to the invention usually results in a mixture of different polyol esters, especially polyglycerol esters, of 3-oxobutyric acid, i.e. in a mixture of at least two, especially at least three different polyol esters, especially polyglycerol esters, of 3-oxobutyric acid. The resulting raw reaction product or raw mixture can be purified by known methods, especially by removing any remaining starting compounds and/or any by-products present, and furthermore—if desired—can be separated by known methods, especially by distillation and/or chromatography (e.g. fractionation into the individual polyol esters, i.e. mono-, di-, tri- etc. polyol esters of 3-oxobutyric acid or else fractionation into fractions with enriched and depleted portions of individual fractions etc.).

Furthermore, the inventive production method does not require enantioselective reaction control, since the formation or release of the active ingredient 3-hydroxybutyric acid in the gastrointestinal tract always takes place in the physiologically relevant form of the R-enantiomer.

According to the invention, it is preferred when, in the general formula (I), the radical $R^1$ represents ethyl.

In other words, according to the invention it is preferred that, as compound of the general formula (I), 3-oxobutyric acid ethyl ester (ethyl 3-oxobutyrate) of the formula $CH_3$—C(O)—$CH_2$—C(O)$OC_2H_5$ is used.

This enables particularly efficient process control and high yields with minimized or suppressed by-product formation. In addition, the 3-oxobutyric acid ethyl ester is also commercially available in large quantities and, moreover, in contrast to the free acid (i.e. 3-oxobutyric acid), is stable and can therefore be used with less effort. Especially, the 3-oxobutyric acid ethyl ester can be obtained on a large scale as a starting compound, e.g. by Claisen condensation of ethyl acetate.

Especially, in the inventive method, the reaction is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the present invention, the reaction can be carried out in the presence of a catalyst, especially an enzyme and/or a metal-containing and/or metal-based, acidic or basic catalyst. In this particular embodiment, it is preferred that the catalyst is recycled after the reaction.

As mentioned hereinabove, according to a particular embodiment of the inventive production method, the reaction may be carried out in the presence of an enzyme as a catalyst.

In this context, the enzyme can especially be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

Within the scope of the present invention, the enzyme used as a catalyst can especially be derived from *Candida antarctica, Mucor miehei* (*Rhizomucor miehei*), *Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially from *Candida antarctica, Mucor miehei* (*Rhizomucor miehei*) and *Thermomyces lanuginosus*.

According to a specific embodiment, the enzyme can be used in immobilized form, immobilized on a carrier, preferentially on a polymeric carrier, preferably on a polymeric organic carrier, more preferably with hydrophobic properties, even more preferably on a poly(meth)acrylic resin-based carrier.

As explained hereinabove with respect to the use of a catalyst in general, when an enzyme is used as a catalyst, it is preferred to recycle the enzyme after the reaction.

If the reaction is carried out in the presence of an enzyme as a catalyst within the framework of the inventive production method, it is preferred if the reaction is carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

In case of using an enzyme as a catalyst, the amount of the enzyme used can vary within a wide range. Especially, the enzyme can be used in amounts, based on the total amount of the starting compounds (I) and (II), in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight.

Nevertheless, it may be necessary to deviate from the above-mentioned amounts in individual cases or for specific applications without leaving the scope of the present invention.

If, according to a particular embodiment of the present invention, the reaction is carried out in the presence of an enzyme as a catalyst, the applied pressure range may also vary within a wide range.

Especially, if the reaction is carried out in the presence of an enzyme as a catalyst, the reaction can be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the present invention, the reaction can be carried out in the presence of a metal-containing and/or metal-based, acidic or basic catalyst According to this alternative embodiment of the present invention, according to which the reaction is carried out in the presence of a metal-containing and/or metal-based, acidic or basic catalyst, the catalyst can especially be selected from (i) basic catalysts, especially alkali or alkaline earth hydroxides and alkali or alkaline earth alcoholates, such as NaOH, KOH, LiH, $Ca(OH)_2$, NaOMe, KOMe and Na(OBu-tert), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

According to this embodiment, especially an alkali or alkaline earth alcoholate can be used as a catalyst.

Especially, also according to this embodiment it is preferred if the catalyst based on the metal-containing and/or metal-based, acidic or basic catalyst is recycled after the reaction.

If, according to the particular embodiment of the present invention the reaction is carried out in the presence of a metal-containing and/or metal-based, acidic or basic catalyst, the temperatures can be varied within a wide range. Especially, the reaction can be carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, also according to this embodiment, the catalyst (i.e. the metal-containing and/or metal-based, acidic or basic catalyst) can also be varied within wide quantity ranges: For example, the catalyst based on a metal-containing and/or metal-based, acidic or basic catalyst can be used in amounts, based on the total amount of the starting compounds (I) and (II), in the range of from 0.01 to 30% by weight, especially in the range of from 0.05 to 15% by weight, preferentially in the range of from 0.1 to 15% by weight, preferably in the range of from 0.2 to 10% by weight Nevertheless, it is possible to deviate from the above-mentioned amounts for specific applications or individual cases without leaving the scope of the present invention.

If, according to this particular embodiment of the present invention, the reaction is carried out in the presence of a metal-containing and/or metal-based, acidic or basic catalyst, the pressure range can equally vary within a wide range: Especially, the reaction can be carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

As far as the quantity of starting materials or starting compounds is concerned, this can also be varied within a wide range.

Taking into account process economy and optimization of the course of the method, especially with regard to the minimization of by-products, it is advantageous if the compound of the general formula (I), based on the hydroxyl groups of the polyol (II), especially polyglycerol, is used in molar amounts in a range of from equimolar amount up to a molar excess of 200 mol-%, especially in a range of from equimolar amount up to a molar excess of 150 mol-%, preferentially in a range of from equimolar amount up to a molar excess of 100 mol-%.

Similarly, taking into account process economy and optimization of the course of the method, especially with regard to minimizing by-products, it is advantageous if the compound of the general formula (I) and the polyol (II), especially polyglycerol, are used in a molar ratio of compound of the general formula (I)/polyol (II) in a range of from 1:1 to 10:1, especially in a range of from 2:1 to 8:1, preferentially in a range of from 3:1 to 6:1.

As far as the polyol (II) usable in the method according to the invention is concerned, it is particularly preferred if the polyol (II) comprises at least three hydroxyl groups (OH-groups)).

According to a special embodiment of the inventive method, it may especially be provided that the polyol (II) corresponds to general formula (IIa)

$$(HO)_m—(X)—(OH)_n \quad \text{(IIa)}$$

wherein, in the general formula (IIa),

X represents an organic radical, especially a preferentially saturated organic radical comprising 4 to 21 carbon atoms and optionally comprising 1 to 9 oxygen atoms, preferentially selected from an alkyl radical or a (poly)alkyl ether radical, especially (poly)alkylene glycol radical, more preferably selected from a $C_4$-$C_{21}$-alkyl radical or a $C_4$-$C_{21}$-(poly)alkyl ether radical, especially a $C_4$-$C_{21}$-(poly) alkylene glycol radical; and the variables m and n, each independently of one another, represent an integer from 1 to 10.

Especially, according to the invention, it is preferred in this context that the hydroxyl groups of the polyol (II) are in any position of the radical X, preferentially wherein at least one hydroxyl group is terminal (i.e. being a primary hydroxyl group). This means in particular that the hydroxyl groups can be located or provided in any position of the organic radical X (preferentially, however, with the proviso that at least one hydroxyl group is terminal and/or is a primary hydroxyl group).

Especially, the polyol (II), which can be used within the scope of the inventive method, may be selected from polyether polyols and alkane polyols and combinations thereof, especially $C_4$-$C_{21}$-polyether polyols and $C_4$-$C_{21}$-alkane polyols, preferentially $C_4$-$C_{21}$-polyether polyols and $C_4$-$C_{21}$-alkane diols, more preferably polyether polyols, even more preferably $C_4$-$C_{21}$-polyether polyols.

According to a particular embodiment of the method according to the invention, the polyol (II) may be selected from polyether polyols, especially $C_4$-$C_{21}$-polyether polyols, preferentially polyglycerols of the general formula (IIb)

$$HO—CH_2—CH(OH)—CH_2—[O—CH_2—CH(OH)—CH_2]_p—OH \quad \text{(IIb)}$$

wherein, in the general formula (IIb), the variable p represents an integer from 1 to 6, especially from 1 to 4, preferentially 1 or 2, more preferably 1.

According to another special embodiment of the method according to the invention, the polyol (II) may be a diglycerol of formula (IIc)

$$HO—CH_2—CH(OH)—CH_2—O—CH_2—CH(OH)—CH_2—OH \quad \text{(IIc)}$$

According to a further particular embodiment of the method according to the invention, the polyol (II) may be selected from alkanediols, especially $C_4$-$C_{21}$-alkanediols, preferentially linear or branched alkanediols, preferably linear or branched $C_4$-$C_{21}$-alkanediols, more preferably linear $C_4$-$C_{21}$-alkanediols, even more preferably linear $C_4$-$C_{21}$-alkanediols having at least one terminal and/or primary hydroxyl group, yet even more preferably pentanediol, especially 1,2-pentanediol.

According to a preferred embodiment of the inventive method, the polyol (II) is not propane-1,2,3-triol, i.e. the polyol (II) is not glycerol.

According to an alternative preferred embodiment of the method of the invention, the polyol (II) is propane-1,2,3-triol, i.e. the polyol (II) is glycerol.

According to a preferred embodiment of the present invention, the present invention according to this aspect of the invention relates to a method for producing polyol esters, especially polyglycerol esters, of 3-oxobutyric acid (beta-oxobutyric acid, 3-oxobutanoic acid), especially a method as described hereinabove, wherein at least one compound of the general formula (I)

$$CH_3—C(O)—CH_2—C(O)OR^1 \quad (I)$$

wherein, in the general formula (I), the radical $R^1$ represents $C_1$-$C_4$ alkyl, especially methyl or ethyl, preferably ethyl, is reacted with at least one polyol (II) comprising at least two hydroxyl groups (OH-groups), especially polyglycerol, wherein the polyol (II) is selected from polyether polyols, especially $C_4$-$C_{21}$-polyether polyols, preferentially polyglycerols of the general formula (IIb)

$$HO—CH_2—CH(OH)—CH_2—[O—CH_2—CH(OH)—CH_2]_p—OH \quad (IIb)$$

wherein, in the general formula (IIb), the variable p represents an integer from 1 to 6, especially from 1 to 4, preferentially 1 or 2, more preferably 1, so that, as a reaction product, one or more 3-oxobutyric acid polyol esters (III), especially 3-oxobutyric acid polyglycerol esters, are obtained.

According to another preferred embodiment of the present invention, the present invention according to this aspect of the invention relates to a method for producing polyol esters, especially polyglycerol esters, of 3-oxobutyric acid (beta-oxobutyric acid, 3-oxobutanoic acid), especially a method as described hereinabove, wherein at least one compound of the general formula (I)

$$CH_3—C(O)—CH_2—C(O)OR^1 \quad (I)$$

wherein, in the general formula (I), the radical $R^1$ represents ethyl, is reacted with at least one polyol (II) comprising at least two hydroxyl groups (OH-groups), especially polyglycerol, wherein the polyol (II) is selected from polyglycerols of the general formula (IIb)

$$HO—CH_2—CH(OH)—CH_2—[O—CH_2—CH(OH)—CH_2]_p—OH \quad (IIb)$$

wherein, in the general formula (IIb), the variable p represents an integer 1 or 2, preferentially 1, so that, as a reaction product, one or more 3-oxobutyric acid polyol esters (III), especially 3-oxobutyric acid polyglycerol esters, are obtained.

The following reaction or synthesis scheme illustrates an approach which is particularly preferred according to the invention (wherein depending on the reaction control, either individual esters or a mixture of two or more of them are obtained):

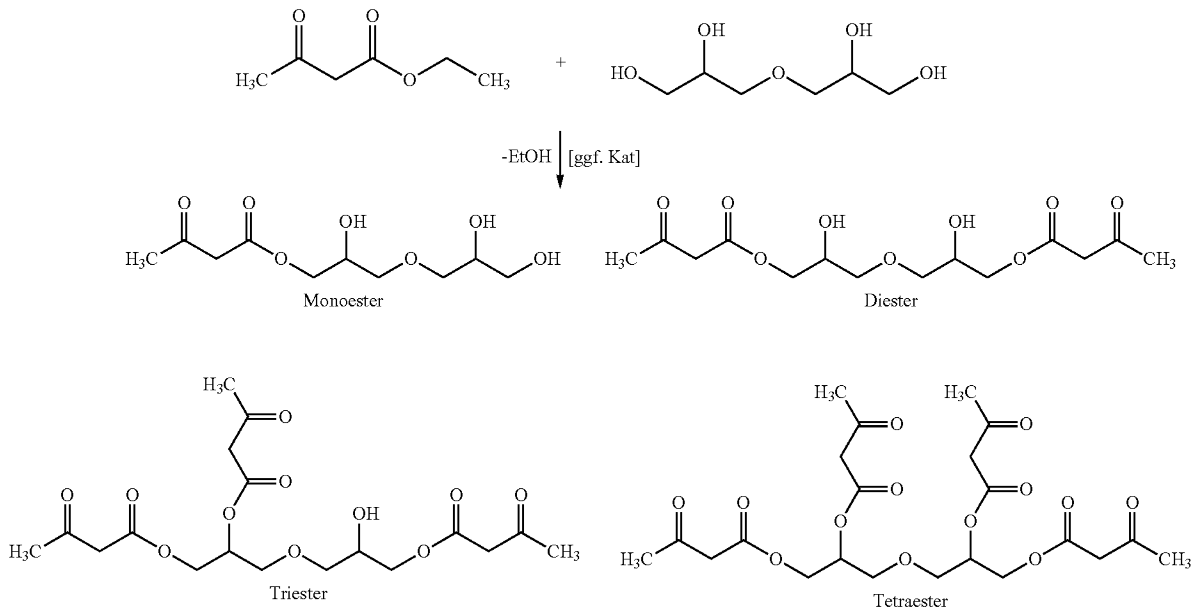

Monoester

Diester

Triester

Tetraester

In the method according to the invention, during the reaction, the compound according to the general formula (IV)

$$R^1—OH \quad (IV)$$

is formed simultaneously, wherein, in the general formula (IV), the radical $R^1$ represents $C_1$-$C_4$ alkyl, especially methyl or ethyl, preferably ethyl.

Especially, it is preferred in this context if the compound according to the general formula (IV) is withdrawn from the reaction, especially continuously withdrawn, especially by means of preferentially continuous removal by distillation. In this way, the reaction equilibrium is efficiently shifted to the side of the reaction products. Also, the formation of by-products is minimized or prevented in this way.

Within the scope of the inventive production method, the reaction product, especially the composition of the reaction product, especially the presence of the various 3-oxobutyric acid polyol esters (III), especially 3-oxobutyric acid polyglycerol esters, and their proportion in the case of a mixture, may be controlled and/or regulated by means of the reaction conditions, especially by selecting the reaction temperature (conversion temperature) and/or by selecting the reaction pressure (conversion pressure) and/or by providing a catalyst and selecting such catalyst with respect to the type and/or amount and/or by selecting the amounts of starting compounds (reactants) and/or by providing the removal of the compound according to the general formula (IV) as defined above.

After the reaction, the reaction product obtained can be subjected to further purification or work-up steps.

In this context, the reaction product obtained can be fractionated after the reaction has been performed, especially fractionated by distillation.

Also, unreacted starting compounds (I) and/or (II) can be separated from the reaction product and subsequently recycled.

According to a special embodiment of the production method according to the invention, it is especially possible to proceed in such a way that hydroxyl groups still present in the reaction product after the reaction has taken place are at least partially, preferentially completely, functionalized, especially esterified. Especially, the reaction can be followed by a partial, especially complete functionalization, especially esterification, of hydroxyl groups still present.

In this particular embodiment of the inventive method, especially the functionalization, especially esterification, of the hydroxyl groups still present in the reaction product after the reaction has taken place can be carried out with at least one carboxylic acid anhydride of the general formula (V)

$$R^3—O—R^3 \qquad (V)$$

wherein, in the general formula (V), the radical $R^3$, each independently of one another, identical or different, represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—; and/or wherein, in the general formula (V), the radical $R^3$ each independently of one another, identical or different, is a fatty acid radical, especially a $C_8$-$C_{34}$-fatty acid radical, preferentially a $C_8$-$C_{34}$-fatty acid radical.

Furthermore, in this particular embodiment of the method according to the invention, it is preferred when the carboxylic acid anhydride of general formula (V) is a fatty acid anhydride, especially a $C_5$-$C_{34}$-fatty acid anhydride, preferentially a $C_8$-$C_{34}$-fatty acid anhydride.

Especially, it is preferred when, as carboxylic acid anhydride of the general formula (V), a compound is used in which the radicals $R^3$ are identical. In other words, as carboxylic acid anhydride of the general formula (V), a symmetrical carboxylic acid anhydride is used.

According to an alternative embodiment, it is preferred when, as carboxylic acid anhydride of the general formula (V), a compound is used in which the radicals $R^3$ are different from one another. In other words, as carboxylic acid anhydride of the general formula (V), an asymmetric carboxylic acid anhydride is used.

According to the invention, the functionalization of the hydroxyl groups still present in the reaction product after the reaction has taken place with the at least one carboxylic acid anhydride of the general formula (V) may be carried out at temperatures in the range of from 60 to 150° C., especially in the range of from 70 to 120° C., preferentially in the range of from 80 to 100° C.

The inventive functionalization of the hydroxyl groups still present in the reaction product after the reaction has taken place with the at least one carboxylic anhydride of the general formula (V) may especially be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

Especially, it is preferred when the functionalization of the hydroxyl groups still present in the reaction product after the reaction has taken place with the at least one carboxylic acid anhydride of the general formula (V) is carried out in the absence of solvents and/or without any solvent. I.e. the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

In the course of the inventive functionalization of the hydroxyl groups still present in the reaction product after the reaction has taken place with the at least one carboxylic acid anhydride of the general formula (V), the compound according to the general formula (VI)

$$R^3—OH \qquad (VI)$$

is formed simultaneously, wherein the radical $R^3$ has the meaning defined hereinabove.

Especially, it is preferred in this context when the compound according to the general formula (VI) is withdrawn during or after the reaction has taken place, especially after the reaction has taken place, preferentially by distillation.

Following the inventive functionalization of the hydroxyl groups still present in the reaction product after the reaction has taken place with the at least one carboxylic acid anhydride of the general formula (V), the product obtained can be subjected to further conventional or per se known purification or work-up steps.

In this context, the functionalization may be followed by a distillation and/or a chromatography, preferentially a distillation.

Especially, any reactants and reaction by-products still present, especially compounds according to the general formula (VI), are distilled off.

Within the course of the functionalization according to the invention, in the case that in the general formula (V) the radicals $R^3$ are different from one another, and/or in the case that in the general formula (V) the radicals $R^3$ each represent an alkyl radical having more than two carbon atoms, the carboxylic acid anhydride of the general formula (V) is obtainable and/or is obtained by reacting acetic anhydride with at least one carboxylic acid, especially fatty acid, of the general formula (VI)

$$R^3—OH \qquad (VI)$$

wherein the radical $R^3$ has the meaning defined hereinabove.

In this context, the reaction of acetic anhydride with the at least one carboxylic acid, especially fatty acid, of the general formula (VI) takes place according to the reaction equation $$[CH_3—C(O)]_2O \quad + \quad 2\,R^3—OH \xrightarrow{-2\,CH_3COOH} R^3—O—R^3$$

wherein the radical $R^3$ has the meaning defined hereinabove, however, with the proviso that the radicals $R^3$ are different from one another and/or that the radicals $R^3$, each independently of one another, represent an alkyl radical having more than two carbon atoms.

According to a particular embodiment of this inventive method, a symmetrical carboxylic anhydride of the general formula (V) is produced. In other words, in the general formula (V), the radicals $R^3$ are identical and represent an alkyl radical having more than two carbon atoms.

According to an alternative particular embodiment of this inventive method, an asymmetric carboxylic acid anhydride of the general formula (V) is produced. Thus, in the general formula (V), the radicals $R^3$ are different from one another, preferentially, in the general formula (V), the radicals $R^3$ each represent an alkyl radical having more than two carbon atoms.

According to an alternative embodiment of the functionalization, especially esterification, of the hydroxyl groups still present in the reaction product after the reaction has taken place, it can be carried out by reaction with at least one carboxylic acid and/or a carboxylic acid ester of the general formula (VII)

$$R^3—O—R^4 \qquad (VII)$$

wherein, in the general formula (VII), the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, the radical $R^4$ represents hydrogen or $C_1$-$C_4$-alkyl, especially methyl or ethyl, preferably hydrogen.

In this context, it is particularly preferred when the carboxylic acid and/or the carboxylic acid ester of the general formula (VII) represents a fatty acid and/or a fatty acid ester, especially a $C_5$-$C_{34}$-fatty acid and/or a $C_5$-$C_{34}$-fatty acid ester, preferentially a $C_8$-$C_{34}$-fatty acid and/or a $C_8$-$C_{34}$-fatty acid ester.

Especially, in this embodiment according to the invention, the functionalization of the hydroxyl groups still present in the reaction product after the reaction has taken place with at least one carboxylic acid and/or a carboxylic acid ester of the general formula (VII) is carried out in the absence of solvents and/or without any solvent. I.e. the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a preferred embodiment, the functionalization of the hydroxyl groups still present in the reaction product after the reaction has taken place with at least one carboxylic acid and/or a carboxylic acid ester of the general formula (VII) is carried out in the presence of a catalyst, especially an enzyme and/or a metal-containing and/or metal-based, acidic or basic catalyst.

In this context, it is particularly preferred if the catalyst is recycled after the reaction.

As previously stated, according to a preferred embodiment, the functionalization of the hydroxyl groups still present in the reaction product after the reaction has taken place with at least one carboxylic acid and/or a carboxylic acid ester of the general formula (VII) can be carried out in the presence of an enzyme as a catalyst.

Especially, the enzyme may especially be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

In this particular embodiment, the enzyme used as catalyst may be derived from *Candida* antarctica, *Mucor miehei* (*Rhizomucor miehei*), *Thermomyces lanuginosus, Candida rugosa, Aspergillus* oryzae, *Pseudomonas cepacia, Pseudomonas fluorescens, Rhizopus delemar* and *Pseudomonas* sp. and combinations thereof, preferentially from *Candida antarctica, Mucor miehei* (*Rhizomucor miehei*) and *Thermomyces lanuginosus.*

In this context, it is particularly preferred when the enzyme is used in immobilized form, especially immobilized on a carrier, preferentially on a polymeric carrier, preferably on a polymeric organic carrier, more preferably with hydrophobic properties, even more preferably on a poly(meth)acrylic resin-based carrier.

As already stated in connection with the catalyst in general, it is preferred when the enzyme is recycled after the reaction.

Insofar as the functionalization of the hydroxyl groups still present in the reaction product after the reaction has taken place with at least one carboxylic acid and/or a carboxylic acid ester of the general formula (VII) is carried out in the presence of an enzyme as a catalyst, it is preferred when the reaction is carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

In the case of using an enzyme as a catalyst, the amount of enzyme used may vary within a wide range. Especially, the enzyme can be used in amounts, based on the total amount of starting compounds, in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight Nevertheless, it may be necessary to deviate from the above-mentioned amounts in individual cases or for specific applications without leaving the scope of the present invention. In this context, the starting compounds are the 3-oxobutyric acid polyol ester (III) and the carboxylic acid and/or the carboxylic acid ester of the general formula (VII).

If, according to a particular embodiment of the present invention, the functionalization of the hydroxyl groups still present in the reaction product after the reaction has taken place with at least one carboxylic acid and/or a carboxylic acid ester of the general formula (VII) is carried out in the presence of an enzyme as catalyst, the pressure range applied can also vary within a wide range.

Especially, when the reaction is carried out in the presence of an enzyme as catalyst, the reaction can be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the inventive functionalization of the hydroxyl groups still present in the reaction product after the reaction has taken place with at least one carboxylic acid and/or a carboxylic acid ester of the general formula (VII), the functionalization can be carried out in the presence of a metal-containing and/or metal-based, acidic or basic catalyst.

According to this alternative embodiment of the functionalization according to the invention, according to which the functionalization is carried out in the presence of a metal-containing and/or metal-based, acidic or basic catalyst, the catalyst can especially be selected from (i) basic catalysts, especially alkali or alkaline earth hydroxides and alkali or alkaline earth alcoholates, such as NaOH, KOH, LiOH, $Ca(OH)_2$, NaOMe, KOMe and Na(OBu-tert), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

In this embodiment, an alkali or alkaline earth alcoholate can especially be used as a catalyst.

Especially, it is also preferred in this embodiment of the functionalization when the catalyst based on the metal-containing and/or metal-based, acidic or basic catalyst is recycled after the reaction.

If, according to this particular embodiment of the present invention, the functionalization of the hydroxyl groups still present in the reaction product after the reaction has taken place with at least one carboxylic acid and/or a carboxylic acid ester of the general formula (VII) is carried in the presence of a metal-containing and/or metal-based acidic or basic catalyst, the temperatures can be varied within a wide range. Especially, the reaction can be carried out in the presence of a metal-containing and/or metal-based acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, also in this embodiment, the catalyst (i.e. the metal-containing and/or metal-based, acidic or basic catalyst) can be varied within wide quantity ranges: Thus, the catalyst based on a metal-containing and/or metal-based, acidic or basic catalyst can be used in amounts, based on the total amount of starting compounds, in the range of from 0.01% by weight to 30% by weight, especially in the range of from 0.05% by weight to 15% by weight, preferentially in the range of from 0.1% by weight to 15% by weight, preferably in the range of from 0.2% by weight to 10% by weight Nevertheless, it is possible to deviate from the above-mentioned amounts for specific applications or individual cases without leaving the scope of the present invention. In this context, the starting compounds are the 3-oxobutyric acid polyol ester (III) and the carboxylic acid and/or the carboxylic acid ester of the general formula (VII).

If, according to this particular embodiment of the present invention, the functionalization of the hydroxyl groups still present in the reaction product after the reaction has taken place with at least one carboxylic acid and/or a carboxylic acid ester of the general formula (VII) is carried out in the presence of a metal-containing and/or metal-based, acidic or basic catalyst, the pressure range can equally vary within a wide range: Especially, the reaction can be carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

In this particular embodiment of the functionalization of the hydroxyl groups still present in the reaction product after the reaction has taken place with at least one carboxylic acid and/or a carboxylic acid ester of the general formula (VII), the compound according to the general formula (VIII)

$$R^4\text{—OH} \qquad \text{(VIII)}$$

is formed simultaneously, wherein the radical $R^4$ has the meaning defined hereinabove.

Especially, it is preferred in this context when the compound of the general formula (VIII) is withdrawn during or after the reaction has taken place, especially during the reaction, preferentially by distillation. In this way, the reaction equilibrium is efficiently shifted to the side of the reaction products. Also, in this way, the formation of by-products is minimized or prevented.

According to a particular embodiment of the method according to the invention, the ester groups introduced in the reaction product (III) by the previously described method may be subjected to a partial transesterification by means of a compound of general formula (VII), as defined hereinabove. In other words, the ester groups introduced in the reaction product (III) by the previously described method may be partially exchanged by means of transesterification by a radical $R^3$ having the meaning defined hereinabove.

In this context, the transesterification according to this particular embodiment of the present invention may be carried out under reaction conditions as previously described for the inventive functionalization of hydroxyl groups still present in the reaction product after the reaction has taken place with at least one carboxylic acid and/or a carboxylic acid ester.

A particularly preferred procedure according to the invention, which intends a functionalization, especially esterification, of hydroxyl groups still present following the reaction, is illustrated by the following reaction or synthesis scheme (wherein, depending on the reaction procedure during the reaction, either individual esters or a mixture of two or more thereof are obtained and wherein, in the following reaction or synthesis scheme, the radical R denotes a radical of the formula $CH_3—(CH_2)_{x=0-28}—C(O)—)$:

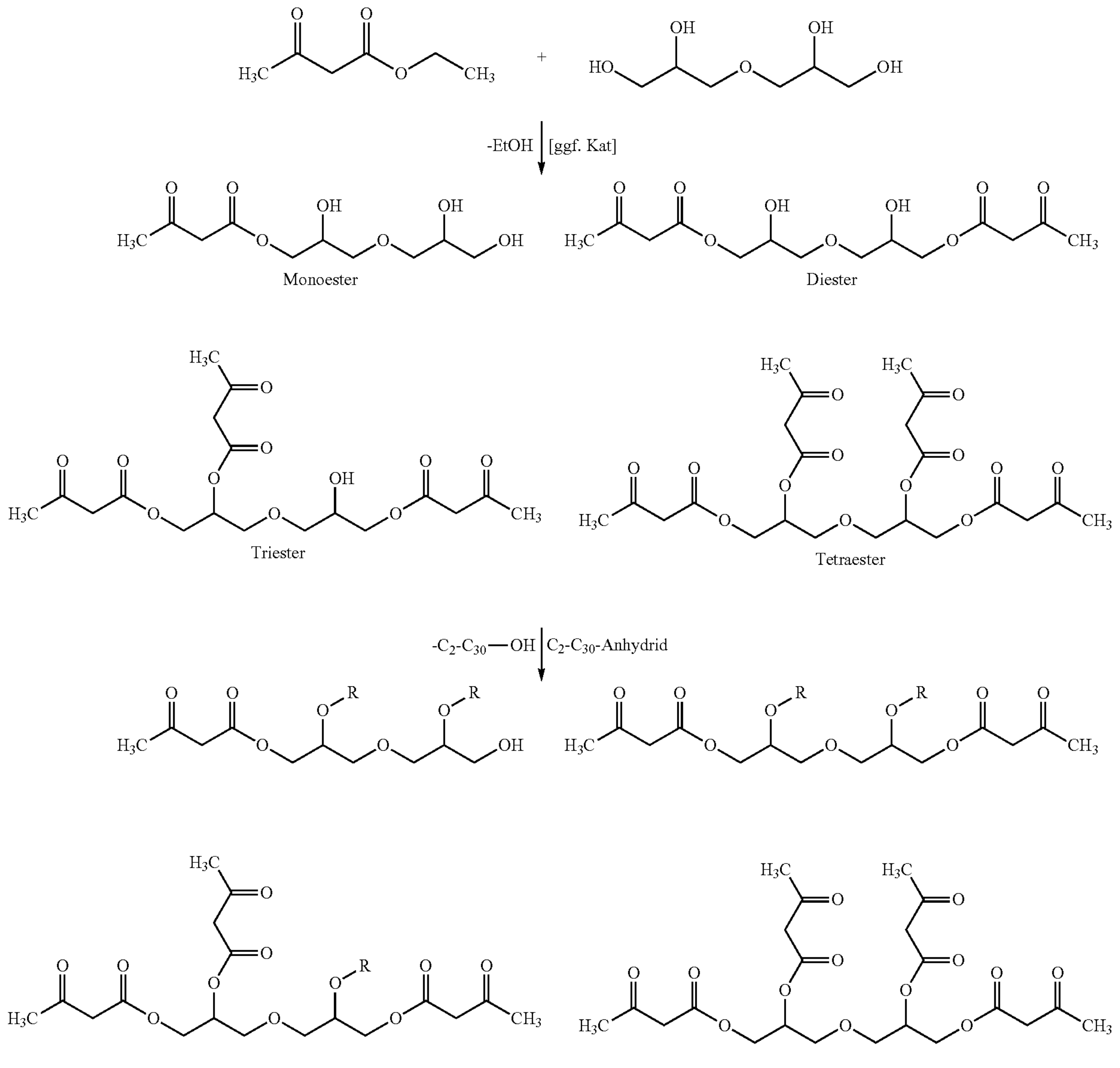

Monoester Diester Triester Tetraester

Furthermore, the present invention relates—according to a second aspect of the present invention—to a method for producing functionalized, especially fatty acid functionalized, polyol esters, especially polyglycerol esters, of 3-oxobutyric acid (beta-oxobutyric acid, 3-oxobutanoic acid), (A) wherein according to a (first) synthesis route (A) initially in a first process step at least one compound of the general formula (I)

$$CH_3—C(O)—CH_2—C(O)OR^1 \quad (I)$$

wherein, in the general formula (I), the radical $R^1$ represents $C_1$-$C_4$-alkyl, especially methyl or ethyl, preferably ethyl, is reacted with at least one polyol (II) comprising at least two hydroxyl groups (OH groups), especially polyglycerol, especially as defined hereinabove, followed by a second process step, wherein the second process step comprises (i) an at least partial functionalization, especially an at least partial esterification, of hydroxyl groups still present by means of at least one fatty acid and/or its ester or anhydride, especially by means of at least one $C_5$-$C_{34}$-fatty acid and/or its ester or anhydride, preferentially by means of at least one $C_8$-$C_{34}$-fatty acid and/or its ester or anhydride, and/or (ii) a partial transesterification of ester groups introduced in the first process step by means of at least one fatty acid and/or its ester, especially by means of at least one $C_5$-$C_{34}$-fatty acid and/or its ester, preferentially by means of at least one $C_8$-$C_{34}$-fatty acid and/or its ester, or else (B) wherein according to a (second, alternative to (A)) synthesis route (B) initially in a first process step at least one polyol (II) comprising at least two hydroxyl groups (OH groups), especially polyglycerol, especially as defined hereinabove, is reacted with at least one fatty acid and/or its ester or anhydride, especially with at least one $C_5$-$C_{34}$-fatty acid and/or its ester or anhydride, preferentially with at least one $C_8$-$C_{34}$-fatty acid and/or its ester or anhydride, followed by a second process step, wherein the second process step comprises (i) an at least partial esterification of hydroxyl groups still present by means of a compound of the general formula (I) as defined hereinabove, and/or (ii) a partial transesterification of ester groups introduced in the first process step by means of a compound of the general formula (I) as defined hereinabove;

so that, as a reaction product, in each case one or more functionalized, especially fatty acid functionalized, preferentially $C_5$-$C_{34}$-fatty acid functionalized, preferably $C_8$-$C_{34}$-fatty acid functionalized, 3-oxobutyric acid polyol esters (III'), preferably one or more functionalized, especially fatty acid functionalized, preferentially $C_5$-$C_{34}$-fatty acid functionalized, preferably $C_8$-$C_{34}$-fatty acid functionalized, 3-oxobutyric acid polyglycerol esters, are obtained.

Especially, the inventive production method according to synthesis route (A) can be carried out according to the inventive method described hereinabove.

According to a particular embodiment of this aspect of the invention, it may especially be provided that, according to synthesis route (B), the polyol (II) is selected from polyether polyols, especially $C_3$-$C_{21}$-polyether polyols, preferentially polyglycerols of general formula (IIb')

$$HO—CH_2—CH(OH)—CH_2—[O—CH_2—CH(OH)—CH_2]_q—OH \quad (IIb')$$

wherein, in the general formula (IIb'), the variable q represents an integer from 0 to 6, especially from 0 to 4, preferentially 0 or 1, more preferably 1.

According to a further particular embodiment of the inventive method, according to synthesis route (B), the polyol (II) may be a diglycerol of formula (IIc)

$$HO—CH_2—CH(OH)—CH_2—O—CH_2—CH(OH)—CH_2—OH \quad (IIc)$$

According to yet another particular embodiment of the inventive method, according to synthesis route (B), the polyol (II) may be propane-1,2,3-triol (glycerol).

According to an alternative particular embodiment of the inventive method, according to synthesis route (B), the polyol (II) is not propane-1,2,3-triol (glycerol).

With regard to the fatty acid and/or fatty acid ester which can be used in the inventive method in accordance with synthesis route (B), it is particularly preferred if the fatty acid and/or the fatty acid ester is a carboxylic acid and/or a carboxylic acid ester of the general formula (VII)

$$R^3—O—R \quad (VII)$$

wherein, in the general formula (VII), the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, the radical $R^4$ represents hydrogen or a $C_1$-$C_4$-alkyl, especially hydrogen, methyl or ethyl, more preferably hydrogen.

Furthermore, with regard to the fatty acid anhydride that can be used in the method of the invention according to synthesis route (B), it is particularly preferred if the fatty acid anhydride is a carboxylic acid anhydride of the general formula (V)

$$R^3—O—R^3 \quad (V)$$

wherein, in the general formula (V), the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—.

Especially, in the inventive method, according to synthesis route (B), in the first process step, the reaction is carried out in the absence of solvents and/or without any solvent. As previously described, this means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the inventive method, according to synthesis route (B), in the first process step, in the case of using fatty acid and/or its ester as starting material, the reaction may be carried out in the presence of a catalyst, especially a metal-containing and/or metal-based, acidic or basic catalyst.

In this context, it is particularly preferred if the catalyst is recycled after the reaction.

Alternatively to this particular embodiment, according to synthesis route (B), in the case of using fatty acid anhydride as starting material, the reaction is carried out in the absence of a catalyst and/or without a catalyst.

As previously described, according to a particular embodiment of the inventive production method, according to synthesis route (B), in the first process step, in the case of using fatty acid and/or its ester as reactant, the reaction can be carried out in the presence of a metal-containing and/or metal-based, acidic or basic catalyst.

The catalyst can be selected from (i) basic catalysts, especially alkali or alkaline earth hydroxides and alkali or alkaline earth alcoholates, such as NaOH, KOH, LiOH, $Ca(OH)_2$, NaOMe, KOMe and Na(OBu-tert), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

In this embodiment, an alkali or alkaline earth alcoholate can especially be used as a catalyst.

Especially, as previously described, it is preferred in this context if the catalyst is recycled after the reaction.

If, according to this particular embodiment, the reaction is carried out in the presence of a metal-containing and/or metal-based, acidic or basic catalyst, it is preferred if the reaction is carried out at temperatures in the range of from 20° C. to 150° C., especially in the range of from 50° C. to 140° C., preferentially in the range of from 70° C. to 130°

C., more preferably in the range of from 80° C. to 125° C., even more preferably in the range of from 100° C. to 120° C.

Especially, according to this embodiment, it is also preferred if the catalyst is used in amounts, based on the total amount of starting compounds, in the range of from 0.01% by weight to 30% by weight, especially in the range of from 0.05% by weight to 15% by weight, preferentially in the range of from 0.1% by weight to 15% by weight, preferably in the range of from 0.2% by weight to 10% by weight.

Furthermore, according to this embodiment, it is preferred if the reaction is carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

Within the scope of the inventive production method, according to synthesis route (B), in the case of using fatty acid and/or its ester as starting material, during the reaction, the compound of the general formula (VIII)

$$R^4—OH \quad (VIII)$$

is formed simultaneously, wherein the radical $R^4$ has the meaning defined hereinabove.

In this context, it is particularly preferred if the compound of the general formula (VIII) is withdrawn during or after the reaction, especially during the reaction, preferably by distillation.

Within the scope of the inventive production method, according to synthesis route (B), in the case of using fatty acid anhydride as starting material, during the reaction, the compound of general the formula (VI)

$$R^3—OH \quad (VI)$$

is formed simultaneously, wherein the radical $R^3$ has the meaning defined hereinabove.

Especially, it is preferred if the compound of the general formula (VI) is withdrawn during or after the reaction, preferably by distillation.

Especially, in the inventive method, according to synthesis route (B), the second process step is also carried out in the absence of solvents and/or without any solvent.

Furthermore, in the inventive method, according to synthesis route (B), the second process step is also carried out in the presence of a catalyst, especially a metal-containing and/or metal-based, acidic or basic catalyst.

Also in this context, it is preferred if the catalyst is recycled after the reaction.

According to another particular embodiment of the present invention, it is preferred if the production method, according to synthesis route (B), also the second process step is carried out in the presence of a metal-containing and/or metal-based, acidic or basic catalyst.

Especially, also according to this particular embodiment, it is preferred if the catalyst is selected from (i) basic catalysts, especially alkali or alkaline earth hydroxides and alkali or alkaline earth alcoholates, such as NaOH, KOH, LiOH, $Ca(OH)_2$, NaOMe, KOMe and Na(OBu-tert), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

In this context, the catalyst used is especially an alkali or alkaline earth alcoholate.

As previously stated, it is particularly advantageous if the catalyst is recycled after the esterification and/or transesterification.

According to this particular embodiment of the inventive method, the temperatures can vary within a wide range. Especially, according to synthesis route (B), the second process step is carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, the amount of catalyst can also be varied according to this particular embodiment: Thus, the catalyst can be used in amounts, based on the total amount of starting compounds, in the range of from 0.01% by weight to 30% by weight, especially in the range of from 0.05% by weight to 15% by weight, preferentially in the range of from 0.1% by weight to 15% by weight, preferably in the range of from 0.2% by weight to 10% by weight.

When, according to this particular embodiment of the present invention, according to synthesis route (B), the second process step is carried out in the presence of a metal-containing and/or metal-based acidic or basic catalyst, the pressure can vary within a wide range: Especially, the second process step may be carried out in the presence of a metal-containing and/or metal-based acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

In this particular embodiment of the inventive method, according to synthesis route (B), in the second process step the compound of the general formula (IX)

$$R^1—O—R^5 \quad (IX)$$

is formed simultaneously, wherein, in the general formula (IX), the radical $R^1$ represents $C_1$-$C_4$-alkyl, especially methyl or ethyl, preferably ethyl, the radical $R^5$, each independently of one another, identical or different, represents hydrogen or a radical $R^3$ as defined hereinabove.

In this context, it is particularly intended that the compound of general formula (IX) is withdrawn during or after the reaction, especially during the reaction, preferentially by distillation.

In the methods according to the invention, according to the first and second aspects of the invention, especially a fatty acid or its derivative, especially ester or anhydride, can be used in the functionalization or esterification or transesterification.

According to the invention, it is especially intended that the fatty acid, preferentially the $C_5$-$C_{34}$-fatty acid, preferably the $C_8$-$C_{34}$-fatty acid, especially in free form or in the form of its ester or anhydride, is selected from the group of caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, lignoceric acid, cerotinic acid, montanic acid, melissic acid, lacceric acid, geddic acid, undecylic acid, myristoleic acid, palmitoleic acid, margaroleic acid, petroselic acid, oleic acid, elaidic acid, vaccenic acid, gadoleic acid, cetoleic acid, erucic acid, nervonic acid, linoleic acid, linolenic acids, calendulic acid, punicic acid, eleostearic acids, stearidonic acid, arachidonic acid, eicosapentaenoic acid, docosadienoic acid, docosatetraenoic acid, docosapentaenoic acid, docosahexaenoic acid, and tetracosahexaenoic acid, as well as mixtures thereof.

According to a particular embodiment of the present invention, it is preferred if the fatty acid, preferably the $C_5$-$C_{34}$-fatty acid, preferentially the $C_8$-$C_{34}$-fatty acid, especially in free form or in the form of its ester or anhydride, is selected from the group of myristic acid, pentadecanoic acid, palmitoleic acid, cetoleic acid, oleic acid, gadoleic acid, cetoleic acid, erucic acid, arachidonic acid, eicosapentaenoic acid, docosadienoic acid, docosatetraenoic acid, docosapentaenoic acid, docosahexaenoic acid, tetracosahexaenoic acid, and mixtures thereof, preferably eicosapentaenoic acid and docosahexaenoic acid, as well as mixtures thereof.

According to a further particular embodiment, the fatty acid, preferentially the $C_5$-$C_{34}$-fatty acid, preferably the $C_8$-$C_{34}$-fatty acid, especially in free form or in the form of its ester or anhydride, is selected from the group of fatty acids based on fish oil and/or occurring in fish oils, especially eicosapentaenoic acid, docosadienoic acid, docosatetraenoic acid, docosapentaenoic acid, docosahexaenoic acid and tetracosahexaenoic acid, as well as mixtures thereof, preferably eicosapentaenoic acid, docosahexaenoic acid, as well as mixtures thereof.

Within the scope of the inventive method(s) according to the two aforementioned aspects of the invention, as a reaction product, one or more optionally functionalized, preferentially optionally fatty acid functionalized, preferably optionally $C_5$-$C_{34}$-fatty acid functionalized, preferentially optionally $C_8$-$C_{34}$-fatty acid functionalized, 3-oxobutyric acid polyol esters (III"), especially 3-oxobutyric acid polyglycerol esters, may be obtained.

Especially, in the inventive method according to the first aspect of the invention, as a reaction product, one or more 3-oxobutyric acid polyol esters (III), especially 3-oxobutyric acid polyglycerol esters, may be obtained.

Furthermore, in the inventive method according to the first or second aspect of the invention, as a reaction product, one or more functionalized, especially fatty acid functionalized, preferably $C_5$-$C_{34}$-fatty acid functionalized, more preferably $C_8$-$C_{34}$-fatty acid functionalized, 3-oxobutyric acid polyol esters (III'), especially 3-oxobutyric acid polyglycerol esters, may be obtained.

Furthermore, the present invention relates—according to a third aspect of the present invention—to a reaction product obtainable according to the inventive method(s). Especially, the reaction product is one or more optionally functionalized, especially optionally fatty acid functionalized, preferentially optionally $C_5$-$C_{34}$-fatty acid functionalized, preferably optionally $C_8$-$C_{34}$-fatty acid functionalized, polyol esters, especially polyglycerol esters, of 3-oxobutyric acid (beta-oxobutyric acid or 3-oxobutanoic acid) or mixtures thereof.

Especially, the reaction product, especially (chemical) product or product mixture, obtainable according to the inventive method(s) may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyol esters (III"), especially 3-oxobutyric acid polyglycerol esters, of the general formula (IIIa")

$$(R^6O)_m—(X)—(OR^6)_n \qquad (IIIa")$$

wherein, in the general formula (IIIa"),

X represents an organic radical, especially a preferentially saturated organic radical comprising 4 to 21 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{21}$-alkyl radical or a $C_4$-$C_{21}$-(poly)alkyl ether radical, especially a $C_4$-$C_{21}$-(poly) alkylene glycol radical, the variables m and n, each independently of one another, represent an integer from 1 to 10, the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C (O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—;

especially wherein the groups $R^6O$— are in any position of the radical X, preferentially wherein at least one group $R^6O$— is terminal.

According to a particular embodiment of the present invention, the reaction product may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyglycerol esters of the general formula (IIIb")

$$R^6O—CH_2—CH(OR^6)—CH_2—[O—CH_2—CH(OR^6)—CH_2]_q—OR^6 \qquad (IIIb")$$

wherein, in the general formula (IIIb"), the variable q represents an integer from 0 to 6, especially from 0 to 4, preferentially 0 or 1, more preferably 1, the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C (O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—.

According to another particular embodiment of the present invention, the reaction product may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyglycerol esters of the general formula ($IIIb_1$")

$$R^6O—CH_2—CH(OR^6)—CH_2—[O—CH_2—CH(OR^6)—CH_2]_p—OR^6 \qquad (IIIb_1")$$

wherein, in the general formula ($IIIb_1$"), the variable p represents an integer from 1 to 6, especially from 1 to 4, preferentially 1 or 2, more preferably 1, the radical $R^6$, each case independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—.

According to yet another particular embodiment of the present invention, the reaction product may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyglycerol esters of the general formula (IIIc")

$$R^6O—CH_2—CH(OR^6)—CH_2—O—CH_2—CH(OR^6)—CH_2—OR^6 \quad \text{(IIIc")}$$

wherein, in the general formula (IIIc"), the radical $R^6$, independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—.

According to an alternative particular embodiment of the present invention, the reaction product may comprise one or more optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid glycerol esters of the general formula (IIId")

$$R^6O—CH_2—CH(OR^6)—CH_2—OR^6 \quad \text{(IIId")}$$

wherein, in the general formula (IIId"), the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—.

According to a particular embodiment of the present invention, the reaction product may especially comprise a mixture of at least two different optionally functionalized, preferentially optionally fatty acid functionalized, preferably optionally $C_8$-$C_{34}$-fatty acid functionalized, especially optionally $C_8$-$C_{34}$-fatty acid functionalized, 3-oxobutyric acid polyol esters (III"), especially 3-oxobutyric acid polyglycerol esters, especially as defined hereinabove.

According to another particular embodiment of the present invention, the reaction product may especially comprise a mixture of at least three different optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyol esters (III"), especially 3-oxobutyric acid polyglycerol esters, especially as defined hereinabove.

In the case that no functionalization or esterification or transesterification is carried out, as a reaction product (i.e. (chemical) product or product mixture), one or more 3-oxobutyric acid polyol esters, especially 3-oxobutyric acid polyglycerol esters, are obtained.

Especially, the reaction product (i.e. (chemical) product or product mixture) obtainable according to the inventive method or the inventive reaction product may comprise one or more 3-oxobutyric acid polyol esters (III), especially 3-oxobutyric acid polyglycerol esters, of the general formula (IIIa)

$$(R^2O)_m—(X)—(OR^2) \quad \text{(IIIa)}$$

wherein, in the general formula (IIIa),

X represents an organic radical, especially a preferentially saturated organic radical comprising 4 to 21 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{21}$-alkyl radical or a $C_4$-$C_{21}$-(poly)alkyl ether radical, especially a $C_4$-$C_{21}$-(poly) alkylene glycol radical, the variables m and n, each independently of one another, represent an integer from 1 to 10, the radical $R^2$, each independently of one another, identical or different, represents: hydrogen or $CH_3$—C(O)—$CH_2$—C(O)—, however, with the proviso that at least one radical $R^2$, especially at least two radicals $R^2$, does not represent hydrogen;

especially wherein the groups $R^2O$— are in any position of the radical X, preferentially wherein at least one group $R^2O$— is terminal.

Especially, the reaction product may comprise one or more 3-oxobutyric acid polyglycerol esters of the general formula (IIIb)

$$R^2O—CH_2—CH(OR^2)—CH_2—[O—CH_2—CH(OR^2)—CH_2]_p—OR^2 \quad \text{(IIIb)}$$

wherein, in the general formula (IIIb), the variable p represents an integer from 1 to 6, especially from 1 to 4, preferentially 1 or 2, more preferably 1, the radical $R^2$, each independently of one another, identical or different, represents: hydrogen or $CH_3$—C(O)—$CH_2$—C(O)—, however, with the proviso that at least one radical $R^2$, especially at least two radicals $R^2$, does not represent hydrogen.

According to a particular embodiment of the present invention, the reaction product may comprise one or more 3-oxobutyric acid polyglycerol esters of the general formula (IIIc)

$$R^2O—CH_2—CH(OR^2)—CH_2—O—CH_2—CH(OR^2)—CH_2—OR^2 \quad \text{(IIIc)}$$

wherein, in the general formula (IIIc), the radical $R^2$, each independently of one another, identical or different, represents: hydrogen or $CH_3$—C(O)—$CH_2$—C(O)—, however, with the proviso that at least one radical $R^2$, especially at least two radicals $R^2$, does not represent hydrogen.

Alternatively, the reaction product obtainable according to the inventive method or the inventive reaction product (i.e. (chemical) product or product mixture) may comprise one or more 3-oxobutyric acid glycerol esters of the general formula (IIId)

$$R^2O—CH_2—CH(OR^2)—CH_2—OR^2 \quad \text{(IIId)}$$

wherein, in the general formula (IIId), the radical $R^2$, each independently of one another, identical or different, represents: hydrogen or $CH_3—C(O)—CH_2—C(O)—$, however, with the proviso that at least one radical $R^2$, especially at least two radicals $R^2$, does not represent hydrogen.

According to a particular embodiment, the reaction product may especially comprise a mixture of at least two different 3-oxobutyric acid polyol esters (III), especially 3-oxobutyric acid polyglycerol esters, especially as defined hereinabove.

Especially, the mixture may have a weight ratio of monoglyceridic esters/di- and higher glyceridic esters in the range of 15-70/30-85, especially in the range of 20-65/35-80.

According to a further particular embodiment, the reaction product may especially comprise a mixture of at least three different 3-oxobutyric acid polyol esters (III), especially 3-oxobutyric acid polyglycerol esters, especially as defined hereinabove.

Especially, the mixture may have a weight ratio of monoglyceridic esters/diglyceridic esters/tri- and higher glyceridic esters in the range of 15-50/35-60/1-35, especially in the range of 20-45/40-55/3-30.

In the case that a functionalization or esterification or transesterification is carried out, as a reaction product (i.e. (chemical) product or product mixture), one or more functionalized, especially fatty acid functionalized, preferably $C_5$-$C_{34}$-fatty acid functionalized, more preferably $C_8$-$C_{34}$-fatty acid functionalized, 3-oxobutyric acid polyol esters, especially 3-oxobutyric acid polyglycerol esters, are obtained.

Especially, the reaction product (i.e. (chemical) product or product mixture) obtainable according to the inventive method may comprise one or more functionalized, especially fatty acid functionalized, preferably $C_5$-$C_{34}$-fatty acid functionalized, more preferably $C_8$-$C_{34}$-fatty acid functionalized, 3-oxobutyric acid polyol esters (III'), especially 3-oxobutyric acid polyglycerol esters, of the general formula (IIIa')

$$(R^6O)_m—(X)—(OR^6)_n \quad \text{(IIIa')}$$

wherein, in the general formula (IIIa'),

X represents an organic radical, especially a preferentially saturated organic radical comprising 4 to 21 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{21}$-alkyl radical or a $C_4$-$C_2$-(poly)alkyl ether radical, especially a $C_4$-$C_{21}$-(poly) alkylene glycol radical, the variables m and n, each independently of one another, represent an integer from 1 to 10, the radical $R^6$, each independently of one another, identical or different, represents: hydrogen, $CH_3—C(O)—CH_2—C(O)—$ or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents $CH_3—C(O)—CH_2—C(O)—$, and with the proviso that at least one radical $R^6$, especially at least two radicals $R^6$, represents a radical $R^3$, as defined hereinabove;

especially wherein the groups $R^6O—$ are in any position of the radical X, preferentially wherein at least one group $R^6O—$ is terminal.

Especially, in the general formula (IIIa'), the radical $R^6$, each independently of one another, identical or different, can represent: $CH_3—C(O)—CH_2—C(O)—$ or a radical $R^3$, as defined hereinabove, however, with the proviso that at least one radical $R^6$, especially at least two radicals $R^6$, represents $CH_3—C(O)—CH_2—C(O)—$ and with the proviso that at least one radical $R^6$ represents a radical $R^3$, as defined hereinabove.

Especially, it is preferred if, in the general formula (IIIa'), the radical $R^6$, each independently of one another, identical or different, does not represent hydrogen.

Especially, the reaction product may comprise one or more functionalized, especially fatty acid functionalized, preferably $C_5$-$C_{34}$-fatty acid functionalized, more preferably $C_8$-$C_{34}$-fatty acid functionalized, 3-oxobutyric acid polyglycerol esters of the general formula (IIIb')

$$R^6O—CH_2—CH(OR^6)—CH_2—[O—CH_2—CH(OR^6)—CH_2]_q—OR^6 \quad \text{(IIIb')}$$

wherein, in the general formula (IIIb'), the variable q represents an integer from 0 to 6, especially from 0 to 4, preferentially 0 or 1, more preferably 1, the radical $R^6$, each independently of one another, identical or different, represents: hydrogen, $CH_3—C(O)—CH_2—C(O)—$ or a radical $R^3$, as defined hereinabove, however, with the proviso that at least two radicals $R^6$ do not represent hydrogen, and with the proviso that at least one radical $R^6$, especially at least two radicals $R^6$, represents $CH_3—C(O)—CH_2—C(O)—$ and with the proviso that at least one radical $R^6$, especially at least two radicals $R^6$, represents a radical $R^3$, as defined hereinabove.

Especially, in the general formula (IIIb'), the radical $R^6$, each independently of one another, identical or different, can represent: $CH_3—C(O)—CH_2—C(O)—$ or a radical $R^3$, as defined hereinabove, however, with the proviso that at least one radical $R^6$, especially at least two radicals $R^6$, represents $CH_3—C(O)—CH_2—C(O)—$ and with the proviso that at least one radical $R^6$ represents a radical $R^3$, as defined hereinabove.

Especially, it is preferred if, in the general formula (IIIb'), the radical $R^6$, each independently of one another, identical or different, does not represent hydrogen According to a particular embodiment of the present invention, the reaction product may comprise one or more functionalized, especially fatty acid functionalized, preferably $C_5$-$C_{34}$-fatty acid functionalized, more preferably $C_8$-$C_{34}$-fatty acid functionalized, 3-oxobutyric acid polyglycerol esters of the general formula ($IIIb_1'$)

$$R^6O—CH_2—CH(OR^6)—CH_2—[O—CH_2—CH(OR^6)—CH_2]_p—OR^6 \quad \text{(IIIb}_1\text{')}$$

wherein, in the general formula ($IIIb_1'$), the variable p represents an integer from 1 to 6, especially from 1 to 4, preferentially 1 or 2, more preferably 1, the radical $R^6$, each independently of one another, identical or different, represents: hydrogen, $CH_3$—C(O)—$CH_2$—C(O)— or a radical $R^3$, as defined hereinabove, however, with the proviso that at least two radicals $R^6$ do not represent hydrogen, and with the proviso that at least one radical $R^6$, especially at least two radicals $R^6$, represents $CH_3$—C(O)—$CH_2$—C(O)— and with the proviso that at least one radical $R^6$, especially at least two radicals $R^6$, represents a radical $R^3$, as defined hereinabove.

Especially, in the general formula ($IIIb_1'$), the radical $R^6$, each independently of one another, identical or different, can represent: $CH_3$—C(O)—$CH_2$—C(O)— or a radical $R^3$, as defined hereinabove, however, with the proviso that at least one radical $R^6$, especially at least two radicals $R^6$, represents $CH_3$—C(O)—$CH_2$—C(O)— and with the proviso that at least one radical $R^6$ represents a radical $R^3$, as defined hereinabove.

Especially, it is preferred if, in the general formula ($IIIb_1'$), the radical $R^6$, each independently of one another, identical or different, does not represent hydrogen According to another particular embodiment of the present invention, the reaction product may comprise one or more functionalized, especially fatty acid functionalized, preferably $C_5$-$C_{34}$-fatty acid functionalized, more preferably $C_8$-$C_{34}$-fatty acid functionalized, 3-oxobutyric acid polyglycerol esters of the general formula (IIIc')

$$R^6O—CH_2—CH(OR^6)—CH_2—O—CH_2—CH(OR^6)—CH_2—OR^6 \quad (IIIc')$$

wherein, in the general formula (IIIc'), the radical $R^6$, each independently of one another, identical or different, represents: hydrogen, $CH_3$—C(O)—$CH_2$—C(O)— or a radical $R^3$, as defined hereinabove, however, with the proviso that at least two radicals $R^6$ do not represent hydrogen, and with the proviso that at least one radical $R^6$, especially at least two radicals $R^6$, represents $CH_3$—C(O)—$CH_2$—C(O)— and with the proviso that at least one radical $R^6$, especially at least two radicals $R^6$, represents a radical $R^3$, as defined hereinabove.

Especially, in the general formula (IIIc'), the radical $R^6$, each independently of one another, identical or different, can represent: $CH_3$—C(O)—$CH_2$—C(O)— or a radical $R^3$, as defined hereinabove, however, with the proviso that at least one radical $R^6$, especially at least two radicals $R^6$, represents $CH_3$—C(O)—$CH_2$—C(O)— and with the proviso that at least one radical $R^6$ represents a radical $R^3$, as defined hereinabove.

Especially, it is preferred if, in the general formula (IIIc'), the radical $R^6$, each independently of one another, identical or different, does not represent hydrogen.

According to an alternative embodiment of the present invention, the reaction product may comprise one or more functionalized, preferably fatty acid functionalized, preferably $C_5$-$C_{34}$-fatty acid functionalized, more preferably $C_8$-$C_{34}$-fatty acid functionalized, 3-oxobutyric acid polyglycerol esters of the general formula (IIId')

$$R^6O—CH_2—CH(OR^6)—CH_2—OR^6 \quad (IIId')$$

wherein, in the general formula (IIId'), the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents $CH_3$—C(O)—$CH_2$—C(O)—, and with the proviso that at least one radical $R^6$, especially at least two radicals $R^6$, represents a radical $R^3$, as defined hereinabove.

Especially, in the general formula (IIId'), the radical $R^6$, each independently of one another, identical or different, can represent: $CH_3$—C(O)—$CH_2$—C(O)— or a radical $R^3$, as defined hereinabove, however, with the proviso that at least one radical $R^6$, especially at least two radicals $R^6$, represents $CH_3$—C(O)—$CH_2$—C(O)— and with the proviso that at least one radical $R^6$ represents a radical $R^3$, as defined hereinabove.

Especially, it is preferred if, in the general formula (IIId'), the radical $R^6$, each independently of one another, identical or different, does not represent hydrogen.

According to a particular embodiment, the reaction product may especially comprise a mixture of at least two different functionalized, especially fatty acid functionalized, preferably $C_5$-$C_{34}$-fatty acid functionalized, more preferably $C_8$-$C_{34}$-fatty acid functionalized, 3-oxobutyric acid polyol esters (III'), especially 3-oxobutyric acid polyglycerol esters, especially as defined hereinabove.

According to a further particular embodiment, the reaction product may especially comprise a mixture of at least three different functionalized, especially fatty acid functionalized, preferably $C_5$-$C_{34}$-fatty acid functionalized, more preferably $C_8$-$C_{34}$-fatty acid functionalized, 3-oxobutyric acid polyol esters (III'), especially 3-oxobutyric acid polyglycerol esters, especially as defined hereinabove.

An object of the present invention is also an optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyol ester (III"), especially 3-oxobutyric acid polyglycerol ester, of the general formula (IIIa")

$$(R^6O)_m—(X)—(OR^6)_n \quad (IIIa")$$

wherein, in the general formula (IIIa"),

X represents an organic radical, especially a preferentially saturated organic radical comprising 4 to 21 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{21}$-alkyl radical or a $C_4$-$C_{21}$-(poly)alkyl ether radical, especially a $C_4$-$C_{21}$-(poly) alkylene glycol radical, the variables m and n, each independently of one another, represent an integer from 1 to 10, the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_1$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—;

especially wherein the groups $R^6O$— are in any position of the radical X, preferentially wherein at least one group $R^6O$— is terminal.

A further object of the present invention is also an optionally functionalized 3-oxobutyric acid polyol ester (III"), especially as described hereinabove, wherein the optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyglycerol ester corresponds to the general formula (IIIb")

$$R^6O—CH_2—CH(OR^6)—CH_2—[O—CH_2—CH(OR^6)—CH_2]_q—OR^6 \quad \text{(IIIb'')}$$

wherein, in the general formula (IIIb"), the variable q represents an integer from 0 to 6, especially from 0 to 4, preferentially 0 or 1, more preferably 1, the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_1$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—.

Again, another object of the present invention is also an optionally functionalized 3-oxobutyric acid polyol ester (III"), especially as described hereinabove, wherein the optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyol ester corresponds to the general formula ($IIIb_1$")

$$R^6O—CH_2—CH(OR^6)—CH_2—[O—CH_2—CH(OR^6)—CH_2]_p—OR^6 \quad \text{(IIIb}_1\text{'')}$$

wherein, in the general formula ($IIIb_1$"), the variable p represents an integer from 1 to 6, especially from 1 to 4, preferentially 1 or 2, more preferably 1, the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_1$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—.

A further object of the present invention is also an optionally functionalized 3-oxobutyric acid polyol ester (III"), especially as described hereinabove, wherein the optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyglycerol ester corresponds to the general formula (IIIc")

$$R^6O—CH_2—CH(OR^6)—CH_2—O—CH_2—CH(OR^6)—CH_2—OR^6 \quad \text{(IIIc'')}$$

wherein, in the general formula (IIIc"), the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least one radical $R^6$, especially at least two radicals $R^6$, does not represent hydrogen, and with the proviso that at least one radical $R^6$, especially at least two radicals $R^6$, represents $CH_3$—C(O)—$CH_2$—C(O)—.

Again, another object of the present invention is also an optionally functionalized 3-oxobutyric acid polyol ester (III"), especially as described hereinabove, wherein the optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyglycerol ester corresponds to the general formula (IIId")

$$R^6O—CH_2—CH(OR^6)—CH_2—OR^6 \quad \text{(IIId'')}$$

wherein, in the general formula (IIId"), the radical $R^6$, each independently of one another, identical or different represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least one radical $R^6$, especially at least two radicals $R^6$, does not represent a hydrogen, and with the proviso that at least one radical $R^6$, especially at least two radicals $R^6$, represents $CH_3$—C(O)—$CH_2$—C(O)—.

A further object of the present invention according to this aspect of the invention, according to a particular embodiment, is a mixture comprising at least two different optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyol esters (III"), especially 3-oxobutyric acid polyglycerol esters, especially as defined hereinabove.

Again, another object of the present invention according to this aspect of the invention is, according to a particular embodiment, a mixture comprising at least three different optionally functionalized, preferentially optionally fatty acid functionalized, preferably optionally $C_5$-$C_{34}$-fatty acid functionalized, especially optionally $C_8$-$C_{34}$-fatty acid functionalized, 3-oxobutyric acid polyol esters (III"), especially 3 oxo-butyric acid polyglycerol esters, especially as defined hereinabove.

According to a further embodiment, also an object of the present invention is a 3-oxobutyric acid polyol ester (111), especially 3-oxobutyric acid polyglycerol ester, of the general formula (IIIa)

$$(R^2O)_m—(X)—(OR^2)_n \quad \text{(IIIa)}$$

wherein, in the general formula (IIIa),

X represents an organic radical, especially a preferentially saturated organic radical comprising 4 to 21 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{21}$-alkyl radical or a $C_4$-$C_{21}$-(poly)alkyl ether radical, especially a $C_4$-$C_{21}$-(poly) alkylene glycol radical, the variables m and n, each independently of one another, represent an integer from 1 to 10, the radical $R^2$, each independently of one another, identical or different, represents: hydrogen or $CH_3$—C(O)—$CH_2$—C(O)—, however, with the proviso that at least one radical $R^2$, especially at least two radicals $R^2$, does not represent hydrogen;

especially wherein the groups $R^2O$— are in any position of the radical X, preferentially wherein at least one group $R^2O$— is terminal.

According to this embodiment, another object of the present invention is a 3-oxobutyric acid polyol ester (III), especially as described hereinabove, wherein the 3-oxobutyric acid polyglycerol ester corresponds to the general formula (IIIb)

$$R^2O—CH_2—CH(OR^2)—CH_2—[O—CH_2—CH(OR^2)—CH_2]_p—OR^2 \quad \text{(IIIb)}$$

wherein, in the general formula (IIIb), the variable p represents an integer from 1 to 6, especially from 1 to 4, preferentially 1 or 2, and more preferably 1, the radical $R^2$, each independently of one another, identical or different, represents: hydrogen or $CH_3$—C(O)—$CH_2$—C(O)—, however, with the proviso that at least one radical $R^2$, especially at least two radicals $R^2$, does not represent hydrogen.

According to this embodiment, an again further subject of the present invention is a 3-oxobutyric acid polyol ester (III), especially as described hereinabove, wherein the 3-oxobutyric acid polyglycerol ester corresponds to the general formula (IIIc)

$$R^2O—CH_2—CH(OR^2)—CH_2—O—CH_2—CH(OR^2)—CH_2—OR^2 \quad \text{(IIIc)}$$

wherein, in the general formula (IIIc), the radical $R^2$, each independently of one another, identical or different, represents: hydrogen or $CH_3$—C(O)—$CH_2$—C(O)—, however, with the proviso that at least one radical $R^2$, especially at least two radicals $R^2$, does not represent hydrogen.

According to this embodiment, an additional embodiment of the present invention is a 3-oxobutyric acid glycerol ester of the general formula (IIId)

$$R^2O—CH_2—CH(OR^2)—CH_2—OR^2 \quad \text{(IIId)}$$

wherein, in the general formula (IIId), the radical $R^2$, each independently of one another, identical or different, represents: hydrogen or $CH_3$—C(O)—$CH_2$—C(O)—, however, with the proviso that at least one radical $R^2$, especially at least two radicals $R^2$, does not represent hydrogen.

Another object of the present invention according to this aspect of the invention according to a further particular embodiment is a mixture comprising at least two different 3-oxobutyric acid polyol esters (III), especially 3-oxobutyric acid polyglycerol esters, especially as defined hereinabove.

Especially, the mixture may have a weight ratio of monoglyceridic esters/di- and higher glyceridic esters in the range of 15-70/30-85, especially in the range of 20-65/35-80.

An again further object of the present invention according to this aspect of the invention according to a further particular embodiment is a mixture comprising at least three different 3-oxobutyric acid polyol esters (Iii), especially 3-oxobutyric acid polyglycerol esters, especially as defined hereinabove.

Especially, the mixture may have a weight ratio of monoglyceridic esters/diglyceridic esters/tri- and higher glyceridic esters in the range of 15-50/35-60/1-35, especially in the range of 20-45/40-55/3-30.

According to a further alternative embodiment, also an object of the present invention is a functionalized, especially fatty acid functionalized, preferably $C_5$-$C_{34}$-fatty acid functionalized, more preferably $C_8$-$C_{34}$-fatty acid functionalized, 3-oxobutyric acid polyol ester (III'), especially 3-oxobutyric acid polyglycerol ester, of the general formula (IIIa')

$$(R^6O)_m—(X)—(OR^6)_n \quad \text{(IIIa')}$$

wherein, in the general formula (IIIa'),

X represents an organic radical, especially a preferentially saturated organic radical comprising 4 to 21 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{21}$-alkyl radical or a $C_4$-$C_{21}$-(poly)alkyl ether radical, especially a $C_4$-$C_{21}$-(poly) alkylene glycol radical, the variables m and n, each independently of one another, represent an integer from 1 to 10, the radical $R^6$, each independently of one another, identical or different, represents: hydrogen, a radical $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents $CH_3$—C(O)—$CH_2$—C(O)—, and with the proviso that at least one radical $R^6$, especially at least two radicals $R^6$, represents a radical $R^3$ as defined hereinabove;

especially wherein the groups $R^6O$— are in any position of the radical X, preferentially wherein at least one group $R^6O$— is terminal.

Especially, in the general formula (IIIa'), the radical $R^6$, each independently of one another, identical or different, can represent: $CH_3$—C(O)—$CH_2$—C(O)— or a radical $R^3$, as defined hereinabove, however, with the proviso that at least one radical $R^6$, especially at least two radicals $R^6$, represents $CH_3$—C(O)—$CH_2$—C(O)— and with the proviso that at least one radical $R^6$ represents a radical $R^3$, as defined hereinabove.

In this particular embodiment, it is advantageous if, in the general formula (IIIa'), the radical $R^6$, each independently of one another, identical or different, does not represent hydrogen.

According to this particular embodiment, another object of the present invention is a functionalized 3-oxobutyric acid polyol ester (III'), especially as described hereinabove, wherein the functionalized, especially fatty acid functionalized, preferably $C_5$-$C_{34}$-fatty acid functionalized, more preferably $C_8$-$C_{34}$-fatty acid functionalized, 3-oxobutyric acid polyglycerol ester corresponds to the general formula (IIIb')

$$R^6O—CH_2—CH(OR^6)—CH_2—[O—CH_2—CH(OR^6)—CH_2]_q—OR^6 \quad \text{(IIIb')}$$

wherein, in the general formula (IIIb'), the variable q represents an integer from 0 to 6, especially from 0 to 4, preferentially 0 or 1, more preferably 1, the radical $R^6$, each independently of one another, identical or different, represents: hydrogen, $CH_3$—C(O)—$CH_2$—C(O)— or a radical $R^3$, as defined hereinabove, however, with the proviso that at least two radicals $R^6$ do not represent hydrogen, and with the proviso that at least one radical $R^6$, especially at least two radicals $R^6$, represents $CH_3$—C(O)—$CH_2$—C(O)— and with the proviso that at least one radical $R^6$, especially at least two radicals $R^6$, represents a radical $R^3$, as defined hereinabove.

Especially, in the general formula (IIIb'), the radical $R^6$, each independently of one another, identical or different, can represent: $CH_3$—C(O)—$CH_2$—C(O)— or a radical $R^3$, as defined hereinabove, however, with the proviso that at least one radical $R^6$, especially at least two radicals $R^6$, represents $CH_3$—C(O)—$CH_2$—C(O)— and with the proviso that at least one radical $R^6$ represents a radical $R^3$, as defined hereinabove.

In this particular embodiment, it is preferred if, in the general formula (IIIb'), the radical $R^6$, each independently of one another, identical or different, does not represent hydrogen.

According to this particular embodiment, an again further object of the present invention is a functionalized 3-oxobutyric acid polyol ester (III'), especially as described hereinabove, wherein the functionalized, especially fatty acid functionalized, preferably $C_5$-$C_{34}$-fatty acid functionalized, more preferably $C_8$-$C_{34}$-fatty acid functionalized, 3-oxobutyric acid polyglycerol ester corresponds to the general formula ($IIIb_1$')

$$R^6O—CH_2—CH(OR^6)—CH_2—[O—CH_2—CH(OR^6)—CH_2]_p—OR^6 \qquad (IIIb_1')$$

wherein, in the general formula ($IIIb_1$'), the variable p represents an integer from 1 to 6, especially from 1 to 4, preferentially 1 or 2, more preferably 1, the radical $R^6$, each independently of one another, identical or different, represents: hydrogen, $CH_3$—C(O)—$CH_2$—C(O)— or a radical $R^3$, as defined hereinabove, however, with the proviso that at least two radicals $R^6$ do not represent hydrogen, and with the proviso that at least one radical $R^6$, especially at least two radicals $R^6$, represents $CH_3$—C(O)—$CH_2$—C(O)— and with the proviso that at least one radical $R^6$, especially at least two radicals $R^6$, represents a radical $R^3$, as defined hereinabove.

Especially, in the general formula ($IIIb_1$'), the radical $R^6$, each independently of one another, identical or different can represent: $CH_3$—C(O)—$CH_2$—C(O)— or a radical $R^3$, as defined hereinabove, however, with the proviso that at least one radical $R^6$, especially at least two radicals $R^6$, represents $CH_3$—C(O)—$CH_2$—C(O)— and with the proviso that at least one radical $R^6$ represents a radical $R^3$, as defined hereinabove.

In this particular embodiment, it is preferred if, in the general formula ($IIIb_1$'), the radical $R^6$, each independently of one another, identical or different, does not represent hydrogen.

According to this particular embodiment, another object of the present invention is a functionalized 3-oxobutyric acid polyol ester (III'), especially as described hereinabove, wherein the functionalized, especially fatty acid functionalized, preferably $C_5$-$C_{34}$-fatty acid functionalized, more preferably $C_8$-$C_{34}$-fatty acid functionalized, 3-oxobutyric acid polyol ester corresponds to the general formula (IIIc')

$$R^6O—CH_2—CH(OR^6)—CH_2—O—CH_2—CH(OR^6)—CH_2—OR^6 \qquad (IIIc')$$

wherein, in the general formula (IIIc'), the radical $R^6$, each independently of one another, identical or different, represents: hydrogen, $CH_3$—C(O)—$CH_2$—C(O)— or a radical $R^3$, as defined hereinabove, however, with the proviso that at least two radicals $R^6$ do not represent hydrogen, and with the proviso that at least one radical $R^6$, especially at least two radicals $R^6$, represents $CH_3$—C(O)—$CH_2$—C(O)— and with the proviso that at least one radical $R^6$, especially at least two radicals $R^6$, represents a radical $R^3$, as defined hereinabove.

Especially, in the general formula (IIIc'), the radical $R^6$, each independently of one another, identical or different, can represent: $CH_3$—C(O)—$CH_2$—C(O)— or a radical $R^3$, as defined hereinabove, however, with the proviso that at least one radical $R^6$, especially at least two radicals $R^6$, represents $CH_3$—C(O)—$CH_2$—C(O)— and with the proviso that at least one radical $R^6$ represents a radical $R^3$, as defined hereinabove.

In this particular embodiment, it is preferred if, in the general formula (IIIc'), the radical $R^6$, each independently of one another, identical or different, does not represent hydrogen.

According to this particular embodiment, an again further object of the present invention is a functionalized 3-oxobutyric acid polyol ester (III'), especially as described hereinabove, wherein the functionalized, especially fatty acid functionalized, preferably $C_5$-$C_{34}$-fatty acid functionalized, more preferably $C_8$-$C_{34}$-fatty acid functionalized, 3-oxobutyric acid polyglycerol ester corresponds to the general formula (IIId')

$$R^6O—CH_2—CH(OR^6)—CH_2—OR^6 \qquad (IIId')$$

wherein, in the general formula (IIId'), the radical $R^6$, each independently of one another, identical or different, represents: hydrogen, $CH_3$—C(O)—$CH_2$—C(O)— or a radical $R^3$, wherein the radical $R^3$ represents a radical of the type linear (straight-chain) or branched, saturated or mono- or polyunsaturated ($C_1$-$C_{33}$-alkyl)-C(O)—, especially ($C_4$-$C_{33}$-alkyl)-C(O)—, preferably ($C_7$-$C_{33}$-alkyl)-C(O)—, however, with the proviso that at least two radicals $R^6$ do not represent hydrogen, and with the proviso that at least one radical $R^6$, especially at least two radicals $R^6$, represents $CH_3$—C(O)—$CH_2$—C(O)—, and with the proviso that at least one radical $R^6$, especially at least two radicals $R^6$, represents a radical $R^3$, as defined hereinabove.

Especially, in the general formula (IIId'), the radical $R^6$, each independently of one another, identical or different, can represent: $CH_3$—C(O)—$CH_2$—C(O)— or a radical $R^3$, as defined hereinabove, however, with the proviso that at least one radical $R^6$, especially at least two radicals $R^6$, represents $CH_3$—C(O)—$CH_2$—C(O)— and with the proviso that at least one radical $R^6$ represents a radical $R^3$, as defined hereinabove.

Especially, it is preferred if, in the general formula (IIId'), the radical $R^6$, each independently of one another, identical or different, does not represent hydrogen.

A further object of the present invention according to this aspect of the invention is, according to a further particular embodiment, a mixture comprising at least two different functionalized, especially fatty acid functionalized, preferably $C_5$-$C_{34}$-fatty acid functionalized, more preferably $C_8$-$C_{34}$-fatty acid functionalized, 3-oxobutyric acid polyol esters (III'), especially 3-oxobutyric acid polyglycerol esters, especially as defined hereinabove.

Another object of the present invention according to this aspect of the invention is, according to another particular embodiment, a mixture comprising at least three different functionalized, especially fatty acid functionalized, preferably $C_5$-$C_{34}$-fatty acid functionalized, more preferably $C_8$-$C_{34}$-fatty acid functionalized, 3-oxobutyric acid polyol esters (III'), especially 3-oxobutyric acid polyglycerol esters, especially as defined hereinabove.

As the applicant has surprisingly found out, the reaction product obtainable according to the inventive method or the inventive reaction product, as defined hereinabove, and/or the 3-oxobutyric acid polyol ester(s), especially 3-oxobutyric acid polyglycerol ester(s), obtainable according to the inventive production method or the inventive 3-oxobutyric acid polyol ester(s), especially 3-oxobutyric acid polyglycerol ester(s), as defined hereinabove, is/are particularly suitable as a precursor or metabolite of acetoacetate (acetoacetate) and ultimately 3-hydroxybutyric acid or its salts, since this precursor or metabolite is, on the one hand, converted physiologically, especially in the gastrointestinal tract, to acetoacetate and ultimately to 3-hydroxybutyric acid or its salts and, on the other hand, simultaneously comprises a good physiological compatibility or tolerability, especially with regard to non-toxicity and acceptable organoleptic properties. Especially, the sustained release of the physiologically active substance (i.e. acetoacetate and ultimately 3-hydroxybutyric acid) in the gastrointestinal tract is advantageous in the medical field, since the active substance 3-hydroxybutyric acid can thus be made available over a longer period of time, thus enabling ketosis therapy. 3-Oxobutyric acid polyol esters have a stronger retarding effect or onset of action than 3-hydroxybutyric acid polyol esters, which means that the time require for releasing the active ingredient in a corresponding therapy is further extended compared to the use of 3-hydroxybutyric acid polyol esters.

Furthermore, the reaction product obtainable according to the inventive method or the inventive reaction product, as defined hereinabove, and/or the 3-oxobutyric acid polyol ester(s), especially 3-oxobutyric acid polyglycerol ester(s), obtainable according to the inventive production method or the inventive 3-oxobutyric acid polyol ester(s), especially 3-oxobutyric acid polyglycerol ester(s), as defined hereinabove, is/are easily accessible or available on a large scale on a synthetic basis, even on a commercial scale, and with the required pharmaceutical or pharmacological quality The reaction product obtainable according to the inventive method or the inventive reaction product, as defined hereinabove, and/or the 3-oxobutyric acid polyol ester(s), especially 3-oxobutyric acid polyglycerol ester(s), obtainable according to the inventive production method or the inventive 3-oxobutyric acid polyol ester(s), especially 3-oxobutyric acid polyglycerol ester(s), as defined hereinabove, thus represents an efficient pharmacological drug target in the context of keto-body therapy of the human or animal body.

In the following, the remaining aspects of the invention are explained in more detail.

Equally, the present invention relates—according to a fourth aspect of the present invention—to a pharmaceutical composition, especially a drug or medicament, which comprises a reaction products obtainable according to the inventive production method or an inventive reaction product, as defined hereinabove, respectively, and/or one or more 3-oxobutyric acid polyol esters obtainable according to the inventive production method and/or one or more inventive 3-oxobutyric acid polyol esters, as defined above, respectively.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomallysosomal storage diseases such as sphingolipidosis, especially Niemann-Pick disease, diabetes mellitus and effects or side-effects of chemotherapy.

Again, a further subject-matter of the present invention—according to a fifth aspect of the present invention—is a reaction products obtainable according to the inventive production method or an inventive reaction product, as defined hereinabove, respectively, and/or one or more 3-oxobutyric acid polyol esters obtainable according to the inventive production method and/or one or more inventive 3-oxobutyric acid polyol esters, as defined above, respectively, for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lysosomal storage diseases such as sphingolipidosis, especially Niemann-Pick disease, diabetes mellitus and effects or side-effects of chemotherapy.

Likewise, a further subject-matter of the present invention—according to a sixth aspect of the present invention—is the use of a reaction products obtainable according to the inventive production method or an inventive reaction product, as defined hereinabove, respectively, and/or one or more 3-oxobutyric acid polyol esters obtainable according to the inventive production method and/or one or more inventive 3-oxobutyric acid polyol esters, as defined above, respectively, for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lysosomal storage diseases such as sphingolipidosis, especially Niemann-Pick disease, diabetes mellitus and effects or side-effects of chemotherapy.

Likewise, a further subject-matter of the present invention—according to a seventh aspect of the present invention—is the use of a reaction products obtainable according to the inventive production method or an inventive reaction product, as defined hereinabove, respectively, and/or one or more 3-oxobutyric acid polyol esters obtainable according to the inventive production method and/or one or more inventive 3-oxobutyric acid polyol esters, as defined above, respectively, for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to a eighth aspect of the present invention—is a food and/or a food product, which comprises a reaction products obtainable according to the inventive production method or an inventive reaction product, as defined hereinabove, respectively, and/or one or more 3-oxobutyric acid polyol esters obtainable according to the inventive production method and/or one or more inventive 3-oxobutyric acid polyol esters, as defined above, respectively.

According to a particular embodiment, the food and/or the food product may essentially be a dietary supplement, a functional food, a novel food, a food additive, a food supplement, a dietary food, a power snack, an appetite suppressant or a strength and/or endurance sport supplement Finally, yet another subject-matter of the present invention—according to an ninth aspect of the present invention—is the use of a reaction products obtainable according to the inventive production method or an inventive reaction product, as defined hereinabove, respectively, and/or one or more 3-oxobutyric acid polyol esters obtainable according to the inventive production method and/or one or more inventive 3-oxobutyric acid polyol esters, as defined above, respectively, in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and non-limiting implementation and configuration of the present invention.

EXAMPLES

Abbreviations Used

PG(2)=diglycerol: HO—$CH_2$—CH(OH)—$CH_2$—O—$CH_2$—CH(OH)—$CH_2$—OH

PG(3)=Polyglycerol: HO—$CH_2$—CH(OH)—$CH_2$—[O—$CH_2$—CH(OH)—$CH_2$]$_2$—OH

Examples of Production

The inventive production method is illustrated by the following examples. The general reaction scheme is shown and explained in the general description section.

Production of 3-Oxobutyric Acid Diglycerol Ester Mixtures 25 g 3-oxobutyric acid ethyl ester (ethyl acetoacetate or acetoacetic ester) and 6.5 g diglycerol are provided in a 100-ml-multi-neck flask with dephlegmator (partial condenser) and distillation bridge.

At a temperature of 50° C., 0.35 g immobilized enzyme (CALB lipase on polymer support, derived from *Candida antarctica, e.* g. Novozyme 435) are added. The reaction mixture is stirred at 50° C. for 24 h. The enzyme is then filtered out and the excess 3-oxobutyric acid ethyl ester is distilled off under vacuum.

The reaction product obtained is a 3-oxobutyric acid diglycerol ester and, after analytical analysis, consists of the following composition: 45% 3-oxobutyric acid mono-diglycerol ester, 48% 3-oxobutyric acid di-diglycerol ester, 7% 3-oxobutyric acid tri-diglycerol ester. The characterization is performed by means of GC, GPC and GC-MS.

In the course of purification, reactants and reaction by-products are removed so that a pure mixture is obtained. Part of the mixture is separated by chromatography to obtain the various diglycerol esters as pure substances (i.e. pure 3-oxobutyric acid mono-diglycerol ester, pure 3-oxobutyric acid di-diglycerol ester and pure 3-oxobutyric acid tri-diglycerol ester). Another part of the mixture is subjected to separation by fractional distillation.

Further Production of 3-Oxobutyric Acid Diglycerol Ester Mixtures 106 g ethyl 3-oxobutyric acid ester (ethyl acetoacetate or acetoacetic acid ester) and 29 g diglycerol are provided in a 250-ml-multi-neck flask equipped with a dephlegmator (partial condenser) and distillation bridge.

At a temperature of 100° C., 1.4 g 30% methanolic NaOMe-solution are added while stirring. The ethanol formed during the reaction is continuously distilled off. After a reaction time of 5 h, the reaction mixture is cooled and washed with NaCl-solution. The crude ester mixture is then dried and the excess ethyl 3-oxobutyric acid ester is distilled off under vacuum.

The reaction product is a 3-oxobutyric acid diglycerol ester with the following composition: 26% 3-oxobutyric acid mono-diglycerol ester, 51% 3-oxobutyric acid di-diglycerol ester, 22% 3-oxobutyric acid tri-diglycerol ester, 1% 3-oxobutyric acid tetra-diglycerol ester. The characterization is performed by means of GC, GPC and GC-MS.

In the course of purification, reactants and reaction by-products are removed so that a pure mixture is obtained. Part of the mixture is separated by chromatography to obtain the various diglycerol esters as pure substances (i.e. pure 3-oxobutyric acid mono-diglycerol ester, pure 3-oxobutyric acid di-diglycerol ester and pure 3-oxobutyric acid tri-diglycerol ester etc.). Another part of the mixture is subjected to separation by fractional distillation.

Further Production of 3-Oxobutyric Acid Diglycerol Ester Mixtures

The preceding experiments are each repeated (with enzyme and with NaOMe as catalyst), however, with different polyols (namely with glycerol, polyglycerol PG(3) and 1,2-pentanediol). Comparable results are obtained. Purification and fractionation are performed in the same way.

More Production Examples

Various polyol components based on polyhydric alcohols (polyols) are enzymatically reacted with ethyl 3-oxobutyric acid ethyl ester (ethyl acetoacetate or acetoacetic ester).

The polyalcohols selected are 1,2-pentanediol and diglycerol PG(2). The respective polyols are reacted at 70° C. for 24 h with immobilized enzyme (CALB lipase on polymer support, derived from *Candida antarctica, e*. g. Novozym® 435 from Sigma-Aldrich or Merck) (in each case 1% by weight enzyme and 40 mol-% excess 3-oxobutycid acid ethyl ester). The aforementioned polyols 1,2-pentanediol and diglycerol PG(2) are each efficiently converted to the desired products by the aforementioned enzyme (Novozym® 435). Comparable results to the previous experiments are obtained. Purification and separation or fractionation are performed in the same way.

The experiments are repeated with sodium methylate (NaOMe) as catalyst instead of the enzymes and at temperatures between 100 and 120° C. Comparable results are obtained. Purification and separation or fractionation are performed in the same way.

Since especially the 3-oxobutyric acid PG(2) esters only have a slightly bitter taste, in particular these esters are an efficient product group for therapeutic applications. Therefore, the preceding experiment with enzyme and diglycerol PG(2) as polyalcohol is performed on a larger scale (2 to 4 kg).

First, the stoichiometric reaction conditions of the previous experiments are applied on a scale of 2 kg (40 mol-% excess 3-oxobutyric acid ethyl ester, 1% by weight enzyme). After 15 h, a portion of the reaction mixture (approx. 200 g) is removed for further testing. This is a mono/di-PG(2) ester mixture. Afterwards, another approx. 1 kg of 3-oxobutyric acid ethyl ester is added. The aim is to produce a full ester. It can be seen that after about 20 to 30 h a constant content of di-PG(2) ester is obtained; the mono-PG(2) ester portion decreases and the tri-PG(2) ester portion increases. Further analyses (GPC) show that a tetra-PG(2) ester has also formed.

After distilling off excess 3-oxobutyric acid ethyl ester, the initially obtained (low-boiling) mono/di-PG(2)-ester mixture has only a slightly bitter taste, while the higher (higher-boiling) di-/tri/tetra-PG(2)-ester mixture has a slightly stronger bitter taste. However, both mixtures are organoleptically acceptable and compatible.

After further purification with removal of residual starting compounds and reaction by-products, a pure mixture with significantly improved organoleptic properties is obtained Functionalization Experiments 1. Production of the Anhydride In a 2,000-ml-multi-neck flask with dephlegmator (partial condenser) and distillation bridge, 860 g heptanoic acid are provided and 445 g acetic anhydride are added at 90° C. while stirring. The reaction mixture is stirred at 130° C. under reflux for 6 h. Then the resulting acetic acid, as well as the excess acetic anhydride, is distilled off under vacuum. A heptanoic acid/heptanoic anhydride mixture is obtained with the following composition: 15% heptanoic acid, 85% heptanoic anhydride. Characterization is performed by means of GC, GPC and GC-MS.

2. Functionalization

In a 100-ml-multi-neck flask with a dephlegmator (partial condenser) and distillation bridge, 25 g of the heptanoic acid anhydride and 5 g of a 3-oxobutyric acid mono-, di-, tri-, tetra-diglycerol mixture prepared according to the invention are provided. The reaction mixture is stirred at 70° C. for 24 h. Then the excess heptanoic anhydride and the resulting heptanoic acid are distilled off by short path distillation. A 3-oxobutyric acid-heptanoic acid-diglycerol ester mixture is obtained.

Comparable functionalization experiments are also carried out with fatty acids and alternatively fatty acid anhydrides and again alternatively fatty acid esters (in each case with eicosapentaenoic acid/docosahexaenoic acid mixture and their anhydrides and esters as well as with oleic acid and its anhydride and ester) and lead in each case to analogous results (i.e. esterification of the free OH— groups), as confirmed by corresponding analytic.

The experiments show that the intended functionalization by reaction with carboxylic acid anhydrides leads to the desired products (i.e. esterification of the free OH-groups), as confirmed by appropriate analytic.

Further Syntheses of Functionalized 3-Oxobutyric Acid Polyol Esters.

As polyols 1,2-pentanediol and diglycerol PG(2) are used. The respective polyols are first reacted with fatty acids and alternatively fatty acid anhydrides and again alternatively fatty acid esters (in each case with eicosapentaenoic acid and docosahexaenoic acid and their anhydrides and esters) with sodium methanolate (NaOMe) as catalyst and at temperatures between 100 and 120° C.; the corresponding fatty acid esterified polyols result, which are further reacted with 3-oxobutyric acid ethyl ester in a second, subsequent method step. The corresponding 3-oxobutyric acid/fatty acid polyol ester mixtures are obtained. Comparable results are obtained by the reverse procedure (i.e. first reaction of the polyols with 3-oxobutyric acid ethyl ester, followed by further reaction with the above-mentioned fatty acids or alternatively their anhydrides and esters).

Physiological Application Tests: In-Vitro Digestion Tests

Digestion Experiments (Splitting or Cleavage Experiments) of Inventive

3-BHB-PG(2)-Ester Mixtures

By means of cleavage experiments it is shown that 3-oxobutyric acid PG(2) esters or their mixtures, including reaction by-products, produced according to the invention, can be cleaved in the human gastrointestinal tract.

The starting mixture used is, on the one hand, a purified mixture of 3-oxobutyric acid mono-diglycerol ester, 3-oxobutyric acid di-diglycerol ester, 3-oxobutyric acid tri-diglycerol ester and 3-oxobutyric acid tetra-diglycerol ester obtained by the inventive method and, on the other hand, a purified mixture of functionalized 3-oxobutyric acid mono-diglycerol ester, functionalized 3-oxobutyric acid di-diglycerol ester and functionalized 3-oxobutyric acid tri-diglycerol ester obtained by the inventive method.

For the cleavage experiments under near-body conditions two media are investigated:

FaSSGF, which simulates the stomach

FaSSIF, which simulates the intestinal tract

Both media are from the company Biorelevant®, Ltd. in Great Britain. In addition, in some experiments porcine pancreas is added (Panzytrat® 40,000, Fa. Allergan).

The results of the cleavage experiments in a FaSSGF or FaSSIF medium with Panzytrat® and without Panzytrat® (both 35° C., 24 h) show that the samples hydrolyze under FaSSGF conditions with Panzytrat® and without Panzytrat®; this is mainly due to the low pH value (pH=1.6) of the medium. Under FaSSIF conditions, a lower conversion using Panzytrat® takes place.

The experiment proves that the starting mixture according to the invention is a suitable physiological precursor for the keto bodies acetoacetate and ultimately 3-hydroxybutyric acid for use in the corresponding keto-body therapies.

Further Digestion Experiments (Cleavage Experiments) of Inventive

3-Oxobutyric Acid-PG(2)-Ester Mixtures

Cleavage Experiments with Pancreatin 2 g of a mixture prepared as described hereinabove based on 3-oxobutyric acid mono-diglycerol ester, 3-oxobutyric acid di-diglycerol ester, 3-oxobutyric acid tri-diglycerol ester and 3-oxobutyric acid tetra-diglycerol ester is dissolved in 50 g water and 0.5 g (1% by weight) pancreatin is added. The pancreatin is used in the form of the commercially available product Panzytrat® 40,000 from the Allergan company. The whole mixture is stirred on a hot plate at 50° C.; the course of the reaction is determined and monitored by continuously recording the acid number over time. The acid number increases over the observation period (cleavage of the 3-oxobutyric acid diglycerol ester mixture). The conversion/time course of the aqueous cleavage of the mixture of esters according to the invention by means of pancreatin, including the increase in the acid number over time, demonstrates the desired decomposition of the educt mixture to the free acid. This is confirmed by appropriate analysis. The experiment also proves that the starting mixture (educt mixture) according to the invention is a suitable physiological precursor for the keto bodies acetoacetate and ultimately 3-hydroxybutyric acid for the corresponding keto-body therapies. The test is repeated and verified on the basis of the individual esters in pure form. Comparable results are obtained, i.e. both the 3-oxobutyric acid mono-diglycerol ester and the 3-oxobutyric acid di-diglycerol ester as well as the 3-oxobutyric acid tri-diglycerol ester and the 3-oxobutyric acid tetra-diglycerol ester are each cleaved by pancreatin.

Further Digestion Experiments (Cleavage Experiments) of Further 3-Oxobutyric Acid Polyol Ester Mixtures According to the Invention.

In addition, the other polyol ester mixtures of 3-oxobutyric acid prepared according to the invention are also subjected to digestion tests in the appropriate manner, as previously described, and yield analogous results.

The previously described cleavage experiments prove that the polyol esters, especially polyglycerol esters, of 3-oxobutyric acid are efficient precursors or metabolites for the keto bodies acetoacetate and ultimately 3-hydroxybutyric acid for use in the corresponding keto-body therapies, especially with regard to their intended effect, which moreover are available in physiologically tolerable or physiologically compatible form.

The invention claimed is:

1. A method for producing polyglycerol esters of 3-oxobutyric acid, wherein at least one compound of general formula (I)

$$CH_3—C(O)—CH_2—C(O)OR^1 \quad (I)$$

wherein, in the general formula (I), the radical $R^1$ represents $C_1$-$C_4$-alkyl, is reacted with at least one polyglycerol of general formula (IIb)

$$HO—CH_2—CH(OH)—CH_2—[O—CH_2—CH(OH)—CH_2]_p—OH \quad (IIb)$$

wherein, in the general formula (IIb), the variable p represents an integer from 1 to 6, wherein the reaction is carried out in the absence of solvents and wherein the reaction is carried out in the presence of an enzyme as a catalyst, wherein the enzyme is used in amounts, based on the total amount of starting compounds (I) and (IIb), in the range of from 0.5% by weight to 10% by weight, wherein the reaction is carried out in the presence of an enzyme as a catalyst at temperatures in the range of from 50° C. to 70° C., wherein the compound of the general formula (I), based on the hydroxyl groups of the polyglycerol (IIb), is used in a molar excess of up to 200 mol-%, so that, as a reaction product, one or more 3-oxobutyric acid polyglycerol esters are obtained, wherein, during reaction, a compound according to general formula (IV)

$$R^1—OH(IV)$$

is formed simultaneously, wherein, in the general formula (IV), the radical $R^1$ represents $C_1$-$C_4$ alkyl, wherein the compound according to the general formula (IV) is continuously withdrawn from the reaction, wherein hydroxyl groups still present in the reaction product after the reaction has taken place are at least partially functionalized via esterification at temperatures in the range of from 60 to 150° C. and in the absence of solvents, wherein the functionalization via esterification is carried out with at least one carboxylic acid anhydride of general formula (V)

$$R^3—O—R^3 \quad (V)$$

wherein, in the general formula (V), the radical $R^3$, each independently of one another, identical or different, represents a radical of the type linear or branched, saturated or mono- or polyunsaturated ($C_1$-$C_{33}$-alkyl)-C(O)—.

2. The method according to claim 1, wherein the enzyme catalyst is recycled after the reaction has been carried out.

3. The method according to claim 1, wherein the ester groups introduced in the reaction product by the method according to claim 1 are subjected to a partial transesterification by means of a compound of general formula (VII)

$$R^3—O—R^4 \quad (VII)$$

wherein, in the general formula (VII), the radical $R^3$ represents a radical of the type linear or branched, saturated or mono- or polyunsaturated ($C_1$-$C_{33}$-alkyl)-C(O)—, the radical $R^4$ represents hydrogen or $C_1$-$C_4$-alkyl.

4. A functionalized 3-oxobutyric acid polyglycerol ester or a mixture of at least two different functionalized 3-oxobutyric acid polyglycerol esters, each prepared according to the method of claim 1.

5. A functionalized 3-oxobutyric acid polyglycerol ester, wherein the functionalized 3-oxobutyric acid polyglycerol ester corresponds to general formula ($IIIb_1''$)

$$R^6O—CH_2—CH(OR^6)—CH_2—[O—CH_2—CH(OR^6)—CH_2]_p—OR^6 \quad (IIIb_1'')$$

wherein, in the general formula ($IIIb_1''$), the variable p represents an integer from 1 to 6, the radical $R^6$, each independently of one another, identical or different, represents: hydrogen, $CH_3—C(O)—CH_2—C(O)—$ or a radical $R^3$, wherein the radical $R^3$ represents a radical of the type linear or branched, saturated or mono- or polyunsaturated ($C_1$-$C_{33}$-alkyl)-C(O)—, however, with the proviso that at least one radical $R^6$ does not represent hydrogen, and with the proviso that at least one radical $R^6$ represents $CH_3—C(O)—CH_2—C(O)—$.

6. The functionalized 3-oxobutyric acid polyglycerol ester according to claim 5, wherein the functionalized 3-oxobutyric acid polyglycerol ester corresponds to general formula ($IIIb_1'$)

$$R^{60}—CH_2—CH\ (OR^6)—CH_2—[O—CH_2—CH(OR^6)—CH_2]_p—OR^6 \quad (IIIb_1')$$

wherein, in the general formula ($IIIb_1'$), the variable p represents an integer from 1 to 6, the radical $R^6$, each independently of one another, identical or different, represents: hydrogen, $CH_3—C(O)—CH_2—C(O)—$ or a radical $R^3$ wherein the radical $R^3$ represents a radical of the type linear or branched, saturated or mono- or polyunsaturated ($C_1$-$C_{33}$-alkyl)-C(O)—, however, with the proviso that at least two radicals $R^6$ do not represent hydrogen, and with the proviso that at least one radical $R^6$ represents $CH_3—C(O)—CH_2—C(O)—$ and with the proviso that at least one radical $R^6$ represents a radical $R^3$ as defined hereinabove.

7. The functionalized 3-oxobutyric acid polyglycerol ester according to claim 5, wherein the functionalized 3-oxobutyric acid polyglycerol ester corresponds to general formula (IIIc')

$$R^6O—CH_2—CH(OR^6)—CH_2—O—CH_2—CH(OR^6)—CH_2—OR^6 \quad (IIIc')$$

wherein, in the general formula (IIIc'), the radical $R^6$, each independently of one another, identical or different, represents: hydrogen, $CH_3—C(O)—CH_2—C(O)—$ or a radical $R^3$ wherein the radical $R^3$ represents a radical of the type linear or branched, saturated or mono- or polyunsaturated ($C_1$-$C_{33}$-alkyl)-C(O)—, however, with the proviso that at least two radicals $R^6$ do not represent hydrogen, and with the proviso that at least one radical $R^6$ represents $CH_3—C(O)—CH_2—C(O)—$ and with the proviso that at least one radical $R^6$ represents a radical $R^3$ as defined hereinabove.

8. A pharmaceutical composition comprising one or more functionalized 3-oxobutyric acid polyglycerol esters according to claim 5.

9. The pharmaceutical composition according to claim 8, wherein the pharmaceutical composition is a drug or medicament.

10. A method for treating a human or an animal suffering from a disease of the human or animal body, wherein the method comprises the administration of an effective amount of at least one functionalized 3-oxobutyric acid polyglycerol ester as defined in claim 5.

11. The method of claim 10, wherein the disease is selected among diseases associated with a disorder of the energy metabolism or diseases associated with a disorder of the keto-body metabolism.

12. The method of claim 11, wherein the disease is selected among craniocerebral trauma, stroke, hypoxia, cardiovascular diseases, myocardial infarction, refeeding syndrome, anorexia, epilepsy, neurodegenerative diseases, dementia, Alzheimer's disease, Parkinson's disease, multiple sclerosis and amyotrophic lateral sclerosis, fat metabolic diseases, glucose transporter defect (GLUT1 defect), VL-FAOD and mitochondriopathies, mitochondrial thiolase defect, Huntington's disease, cancers, T-cell lymphomas, astrocytomas and glioblastomas, HIV, rheumatic diseases, rheumatoid arthritis and arthritis urica, diseases of the gastrointestinal tract, chronic inflammatory bowel diseases, ulcerative colitis and Crohn's disease, lysosomal storage diseases, sphingolipidosis, Niemann-Pick disease, diabetes mellitus and effects or side-effects of chemotherapy.

13. A food or a food product comprising at least one functionalized 3-oxobutyric acid polyglycerol ester according to claim 5.

14. A method for producing polyglycerol esters of 3-oxobutyric acid, wherein at least one compound of general formula (I)

$$CH_3—C(O)—CH_2—C(O)OR^1 \quad (I)$$

wherein, in the general formula (I), the radical $R^1$ represents $C_1$-$C_4$-alkyl, is reacted with at least one polyglycerol of general formula (IIb)

$$HO—CH_2—CH(OH)—CH_2—[O—CH_2—CH(OH)—CH_2]_p—OH \quad (IIb)$$

wherein, in the general formula (IIb), the variable p represents an integer from 1 to 6, wherein the reaction is carried out in the absence of solvents and wherein the reaction is carried out in the presence of an enzyme as a catalyst, wherein the enzyme catalyst is recycled after the reaction has been carried out, wherein the enzyme is used in amounts, based on the total amount of starting compounds (I) and (IIb), in the range of from 0.5% by weight to 10% by weight, wherein the reaction is carried out in the presence of an enzyme as a catalyst at temperatures in the range of from 50° C. to 70° C., wherein the compound of the general formula (I), based on the hydroxyl groups of the polyglycerol (IIb), is used in a molar excess of up to 200 mol-%, so that, as a reaction product, one or more 3-oxobutyric acid polyglycerol esters are obtained, wherein, during reaction, a compound according to general formula (IV)

$$R^1—OH \quad (IV)$$

is formed simultaneously, wherein, in the general formula (IV), the radical $R^1$ represents $C_1$-$C_4$ alkyl, wherein the compound according to the general formula (IV) is continuously withdrawn from the reaction, wherein hydroxyl groups still present in the reaction product after the reaction has taken place are at least partially functionalized via esterification at temperatures in the range of from 60 to 150° C. and in the absence of solvents, wherein the functionalization via esterification is carried out with at least one carboxylic acid anhydride of general formula (V)

$$R^3—O—R^3 \quad (V)$$

wherein, in the general formula (V), the radical $R^3$, each independently of one another, identical or different, represents a radical of the type linear or branched, saturated or mono- or polyunsaturated ($C_1$-$C_{33}$-alkyl)-C(O)—.

* * * * *